(12) United States Patent
Stroia et al.

(10) Patent No.: US 12,370,280 B2
(45) Date of Patent: Jul. 29, 2025

(54) ULTRAVIOLET CLEANING OF CARRIERS IN A DRIVE-UP BANKING SYSTEM

(71) Applicant: Hamilton Safe, Mason, OH (US)

(72) Inventors: V. John Stroia, Loveland, OH (US); Todd Lefevers, Hamilton, OH (US); William Harvey Detherage, Amelia, OH (US)

(73) Assignee: Hamilton Safe, Mason, OH (US)

( * ) Notice: Subject to any disclaimer, the term of this patent is extended or adjusted under 35 U.S.C. 154(b) by 676 days.

(21) Appl. No.: 17/832,213

(22) Filed: Jun. 3, 2022

(65) Prior Publication Data
US 2022/0387644 A1    Dec. 8, 2022

Related U.S. Application Data

(60) Provisional application No. 63/196,759, filed on Jun. 4, 2021.

(51) Int. Cl.
*A61L 2/24*    (2006.01)
*A61L 2/10*    (2006.01)
*A61L 2/26*    (2006.01)

(52) U.S. Cl.
CPC .......... *A61L 2/24* (2013.01); *A61L 2/10* (2013.01); *A61L 2/26* (2013.01); *A61L 2202/11* (2013.01); *A61L 2202/14* (2013.01); *A61L 2202/23* (2013.01)

(58) Field of Classification Search
CPC ..... A61L 2/10; A61L 2/24; A61L 2/26; A61L 2202/11; A61L 2202/14; A61L 2202/23; B65G 51/04; B65G 51/18; B65G 51/26
See application file for complete search history.

(56) References Cited

U.S. PATENT DOCUMENTS

| | | | |
|---|---|---|---|
| 5,735,644 A | 4/1998 | Grosswiller et al. |
| 7,424,340 B2 | 9/2008 | Owens |
| 8,256,997 B2 | 9/2012 | Brown |
| 9,433,980 B1 | 9/2016 | Dahl |
| 9,439,996 B2 | 9/2016 | Gross |

FOREIGN PATENT DOCUMENTS

| | | |
|---|---|---|
| CN | 209312171 U | 8/2019 |
| CN | 111899441 A | 11/2020 |
| CN | 202010705879 A | 11/2020 |
| DE | 102016215447 B3 | 11/2017 |

*Primary Examiner* — Lessanework Seifu
(74) *Attorney, Agent, or Firm* — Taft Stettinius & Hollister LLP

(57) ABSTRACT

Apparatuses, methods, and systems for a light kit assembly to disinfect a carrier between banking transactions of a drive-through banking system. Customers or bankers can activate the sanitization mode of operation to kill germs and viruses without removal of the carrier from the drive-through banking system. The sanitization mode of operation can be automatic. The carrier is positioned in the carrier pocket of a customer station in which a light kit assembly has been installed. An indicator light positioned exteriorly of the customer station indicates that the carrier is being sanitized by one or more UV lights attached to a mounting plate having two bi-folded wings that is positioned within the carrier pocket adjacent to the carrier. Two mounting plates in a mirror-image arrangement may be positioned in the carrier pocket to enable 360 degree application of UV light onto the carrier.

20 Claims, 22 Drawing Sheets

```
                                                                    ┌─────── 12" ──────┐
                                                                    │                  │
                                   ──────────── To J11 PIN #3 ──────┘
120VAC in:          White:
         Line ──── Black ──────── To Power Supply AC N ──────── 30"
                   18 Ga 600V
         Neutral ── White
                    18 Ga 600V
                                                          ┌──── 30" ────┐
                                                          │             │
                   Wire:    Description:
                   Black ── To J11 PIN #1 ────────────────┘
                   White ── To Power Supply AC Line N
                            18 Ga 600V Wire Color:  Description:
                   Black ────── To Power Supply AC Line in
                   Black ────── 120 VAC Input
                                Input
                   Red ──────── To Blue Indicator LED
                   Red ──────── 12VDC + from J14

┌───── 10" ─────┐
                   Wire:   Description:                │               │
                   Red ─── To J11 PIN #6 ──────────────┘
                   Black ─ To Blue Light
                   18 Ga
                                                  ┌──── 48" ────┐
                                                  │             │ 3"
                   Wire:   Description:
                   Red ─── To J11 PIN #4
                   Black ─ To J14 PIN #2
                   18 Ga
```

| | | |
|---|---|---|
| Connector AMP #3-520107-2 | 5" | Connector AMP #3-520141-2 |
| Connector AMP #3-520107-2 | 5" | Connector AMP #3-520141-2 |

| Connector AMP #770333-1 Sockets AMP #794016-1 | Power Supply AC Input: AC Line AC Neutral |
|---|---|

| Connector AMP #1-480704-D Sockets AMP #350550-2 | J11: PIN #1 PIN #2 PIN #3 PIN #4 PIN #5 PIN #6 |
|---|---|

| Connector AMP #643817-2 | J14 12VDC: 12VDC + PIN #1 12VDC + PIN #2 |
|---|---|

| Connector AMP #770342-1 Connector AMP #794016-1 | Blue Indicator Light: 12VDC + 12VDC - |
|---|---|

FIG. 12

ULTRAVIOLET CLEANING OF CARRIERS IN A DRIVE-UP BANKING SYSTEM

CROSS-REFERENCE TO RELATED APPLICATION

The present application claims the benefit of the filing date of U.S. Provisional Application No. 63/196,759 filed on Jun. 4, 2021, which is incorporated herein by reference.

BACKGROUND

Field of the Invention

The present disclosure generally relates to an ultraviolet light system for disinfecting a carrier in a drive-through banking system, and more particularly, but not exclusively to disinfecting the carrier that can travel between teller and customer stations of the drive-through banking system under certain conditions.

Description of Related Art

Drive-up banking allows customers the convenience of being able to perform banking transactions with tellers inside the bank without having to leave their automobiles or enter the bank building. A carrier is positioned within a drive-through banking tube that travels between a teller station inside the bank and a customer station that is exterior of the bank in which the customer's automobile or customer is positioned adjacent to. The customer and banker exchange money, coins, deposit slips, identification, and other items necessary to complete a transaction wherein these items are transported in the carrier that travels between the customer and the teller stations. The carrier in the drive-through banking system is typically designed to transport up to 25 pounds of weight between the customer and the teller stations.

One problem with this system is that these carriers are frequently contaminated and dirty because many people handle these carriers, and these carriers transport money and coins which are very dirty materials. As the dirty money and coins are transported within the carrier, the carrier becomes a repository for all the various germs, bacteria, viruses, and dirt on the money and coins as well as from the individuals who handle these items may be carrying. As a result, the carriers can be a potential transmitter of disease.

It is known to remove carriers periodically from the drive-through banking system to wash and clean the carriers. While the carrier is removed, the drive-through banking system is not operable which means that customers cannot be serviced for some period of time until the carrier is returned and assembled with the drive-through banking system. After a dirty carrier is removed, it must be cleaned which is typically done off-site from the bank with a cleaning solution and then the wet carrier is dried. The clean carrier is then returned to the drive-through banking system at a later date. Alternatively, a replacement carrier can be placed in the drive-through banking system while the dirty carrier is being cleaned. However, while the dirty carriers are being cleaned the replacement carrier then becomes dirty with germs, bacteria, viruses, and dirt. Moreover, it is costly to service the carriers by one or more technicians that must retrieve, clean, dry, and return the carriers. Thus, it would be highly desirable if the drive up banking carriers could be regularly sanitized to reduce their ability to transmit bacteria and other diseases without removal of the carrier from the drive-through banking system or interruption of banking services to bank customers. It is also highly desirable to sanitize the carriers after every transaction or as desired by customers and/or bankers to reduce the spread of germs, bacteria, and viruses. Thus, there remains a significant unmet need for the unique apparatuses, methods, systems and techniques disclosed herein.

BRIEF SUMMARY OF THE DISCLOSURE

Unique apparatuses, methods, and systems are disclosed for a light kit assembly that is installed with a teller station or a customer station of a drive-through banking system or a retrofit light kit assembly that is installed with a previously built drive-through banking system. These light kit assemblies are configured to provide automated or manual disinfection and/or sanitization of outside surfaces of carriers that are installed in the drive-through banking system to keep tellers, associates, and customers safe such that the carriers can be disinfected at any time during non-operation of the carrier or while the carrier is not moving. Carriers are configured to hold the goods, cash, coins, banking documents, and typically can hold up to about 25 pounds of weight. The carrier travels in a bank shoot between an operator's unit which is typically at the teller station inside a bank building and a customer's unit which is typically exterior to the bank building. The light kit assembly includes one or more light sources such as UV lamps, UVC lamps, and/or UVC LED strips attached to one or more mounting plates. The light kit assembly is attached to side panels of a carrier pocket of either the customer station or the teller station that receives the carrier therein. In one form, the light kit assembly is attached to the customer station and sanitizes the carrier pocket within the customer station. In another form, the light kit assembly is assembled as retrofit wherein the light kit assembly is installed in a carrier pocket assembly that is then installed into an existing teller or customer station by simply removing an outer cover panel of the existing teller or customer station, removing the old carrier pocket, and inserting the retrofit light kit assembly/carrier pocket assembly.

The light sources on the mounting plates are positioned to emit UV wavelengths and/or radiation onto the carrier and the carrier pocket to sanitize the carrier and carrier pocket by exposing both to ionized and/or non-ionized radiation for a time period effective for inactivating the bacteria or viruses that may be present on the outer surface of the carrier and carrier pocket. Non-ionized radiation includes UV light. The unique shape of the mounting plates with unique placement of the light sources attached to the mounting plates and unique placement of two of the mounting plates on opposite side panels of the carrier pocket emit UV light that covers 360 degrees around the carrier to sanitize the exterior surface area of the carrier and the air within the carrier pocket.

When the drive-up lane is open and in a normal operation mode, the light source is turned OFF. Normal operation mode indicates that the carrier is operable to move between the customer station and the teller station and the carrier is accessible for use by customers or bankers. When sanitization of the carrier is desired, the carrier is returned or positioned in the carrier pocket of the customer unit and the drive-up lane is activated to the night or sanitizing mode of operation. It is contemplated that either the teller at the teller station or the customer at the customer station can manually activate the sanitizing mode. In one form, the night or sanitizing lock button on the teller unit is turned ON manually to activate the sanitizing mode. In another form, after a transaction is complete such that the carrier has traveled between the customer station and the teller station or the carrier has been used by a person, then the sanitizing mode of operation is automatically activated. In the sanitizing mode of operation, the carrier is in the carrier pocket of the customer unit, the customer unit door is closed, and thereafter the light sources are turned ON. Optionally an indicator light positioned on an outer face of the customer unit is turned ON. This indicator light maybe a designated color when illuminated to indicate that the sanitizing process has started. For example, the designated color can be blue, red, or green. The customer unit door of the carrier pocket will close before the light source is turned ON to avoid exposing any person to the UV wavelengths and/or radiation. The light source will remain turned ON for a set time period to sanitize the carrier and the carrier pocket. In one form, the set time period is about 3 minutes however a longer or shorter set time period may be provided to adequately sanitize the carrier and the carrier pocket. In another form, the set time period is about 45 seconds. When sanitization of the carrier is complete, the carrier will then be sent to the operator or teller unit and the lane will return to normal operating mode. Alternatively, upon completion of sanitization or interruption of sanitization, the carrier can remain in the customer unit. If desired, sanitizing can be interrupted or stopped by turning OFF the night or sanitizing mode switch. The set time period will then be interrupted or stopped and the light source will be turned OFF and thereafter the customer unit door will be operable to open and expose the carrier in the carrier pocket.

Beneficially, the light kit assembly is used to disinfect the carrier between transactions by different persons to kill germs and viruses without removal of the carrier from the drive-through banking system. Therefore, there is less down time of the drive-through banking system because the carrier does not need to be removed for cleaning. Moreover, the carrier and carrier pocket can be disinfected after every use which also leads to improved cleanliness for customers and employees. The light kit assembly reduces transmission of bacteria, viruses and other pathogens via the carrier. In one form, for a set time period of 3 minutes the light source including UVC germicidal LED strips emit 275 nm wavelengths can achieve 99.9% sanitizing effect of the carrier and at approximately 45 seconds, the light kit assembly can sanitize approximately 85% of the carrier's outer surface. Beneficially, there is about 80% energy savings with a light source that includes LED over other forms. Beneficially, there are about 10,000 service hours or 2½ year lane operation with a light source that includes one or more LED's.

This summary is provided to introduce a selection of concepts that are further described below in the illustrative embodiments. This summary is not intended to identify key or essential features of the claimed subject matter, nor is it intended to be used as an aid in limiting the scope of the claimed subject matter. Further embodiments, forms, objects, features, advantages, aspects, and benefits shall become apparent from the following description and drawings.

BRIEF DESCRIPTION OF THE DRAWINGS

The description herein makes reference to the accompanying drawings wherein like reference numerals refer to like parts throughout the several views, and wherein:

FIG. 12 is a second illustration of the wire harness input of the FIG. 11 embodiment.

DESCRIPTION OF ILLUSTRATIVE EMBODIMENTS

Figure 1:
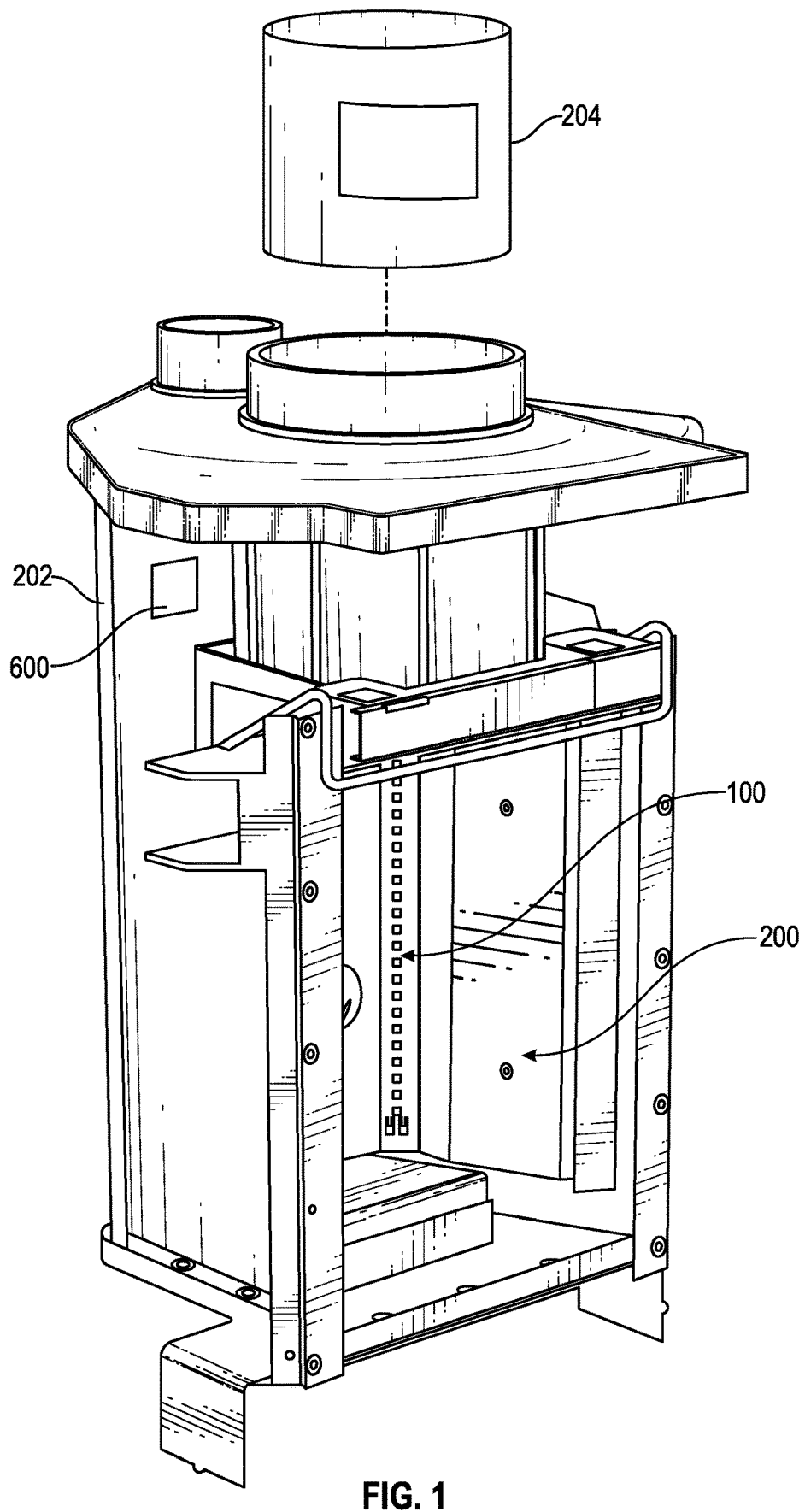
FIG. 1 is a perspective view of a light kit assembly positioned in a customer unit with a carrier.

For the purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated embodiments, and any further applications of the principles of the invention as illustrated therein as would normally occur to one skilled in the art to which the invention relates are contemplated herein.

Figure 2:
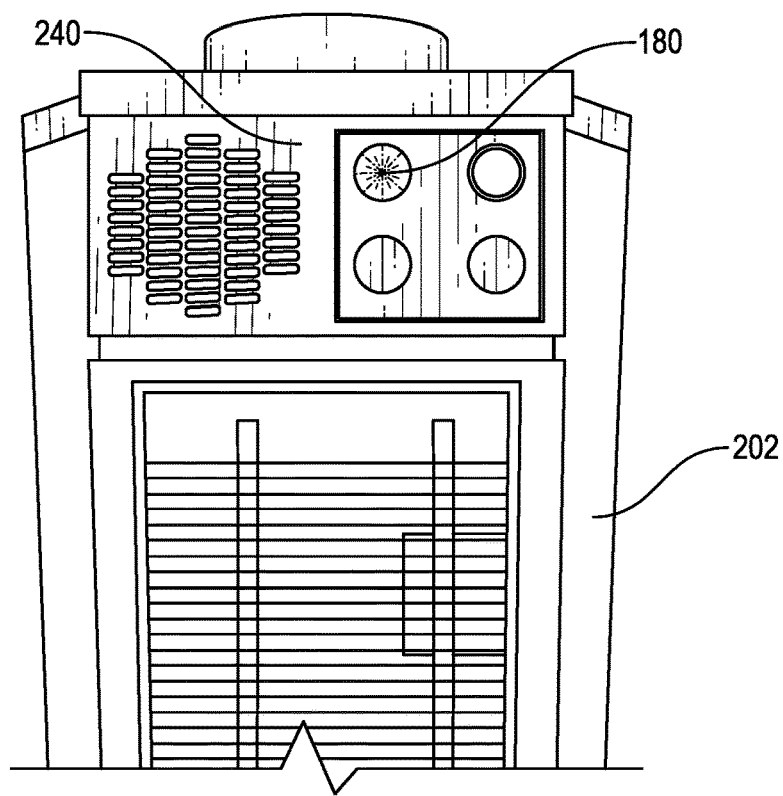
FIG. 2 is a partial front view of the of the FIG. 1 embodiment.
Figure 3:
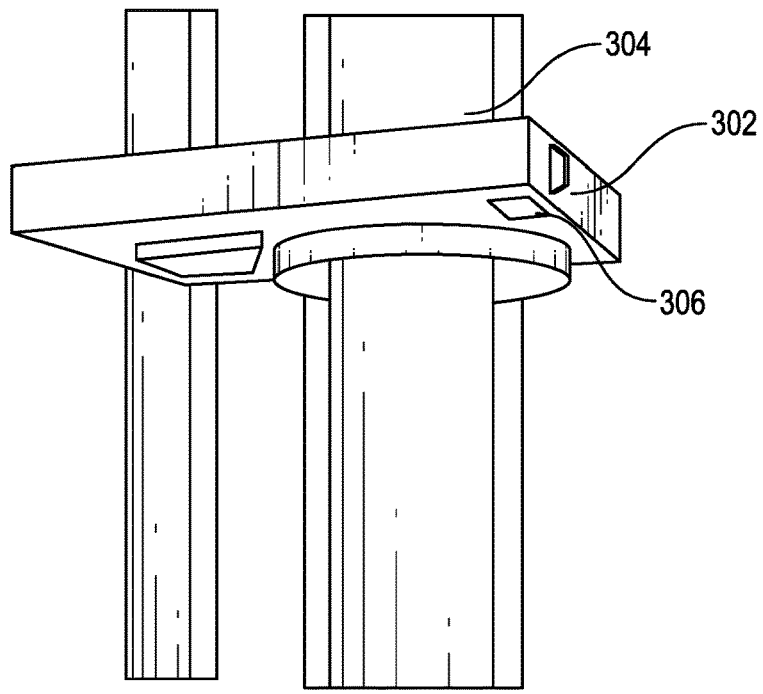
FIG. 3 is a perspective view of a teller unit that is operably connected to the FIG. 1 embodiment.

Referring to FIGS. 1 and 2 is a first embodiment of a light kit assembly 100 assembled within a carrier pocket 200 of a customer unit 202 that receives a carrier or cylinder 204 therein that is configured to hold goods, money, and other banking items. One embodiment of the carrier or cylinder 204 is illustrated above the customer unit 202, however the customer unit 202 is assembled with a bank shoot 304 (not illustrated) through which the carrier 204 travels between the customer unit 202 and a teller station 302. Other forms of the carrier 204 can be used to travel in the bank shoot 304 between the customer unit 202 and the teller station 302. The light kit assembly 100 provides an automated or manual disinfection or sanitization process at a drive-thru banking location to keep persons safe from germs or diseases during the transfer of cash and goods in the carrier 204 that travels between the customer station or unit 202 and the teller station or unit 302 as illustrated in FIG. 3. The teller unit 302 is typically inside a banking facility or building. The teller unit 302 includes a night or sanitizing lock switch 306 that enables someone to manually operate the light kit assembly 100. The customer unit 202 is connected to the teller unit 302 via a bank shoot 304 (partially illustrated in FIG. 3) which is a drive-through banking transit tube that holds the carrier 204 as it travels between the customer unit 202 and the teller unit 302.

It shall be appreciated that the illustrated configuration and components of the light kit assembly 100 are one example embodiment, and that the disclosure contemplates that a variety of different light kit assemblies 100 and associated components thereof may be utilized. It is also contemplated that the light kit assembly 100 can be positioned in the teller unit 302, the customer unit 202, or another location in the drive-through banking transit tube. The light kit assembly 100 can also be a retrofit assembly that is positioned in the teller unit 302 or the customer unit 202 wherein the retrofit assembly may include different connections to units 302 or 202.

Figure 4:
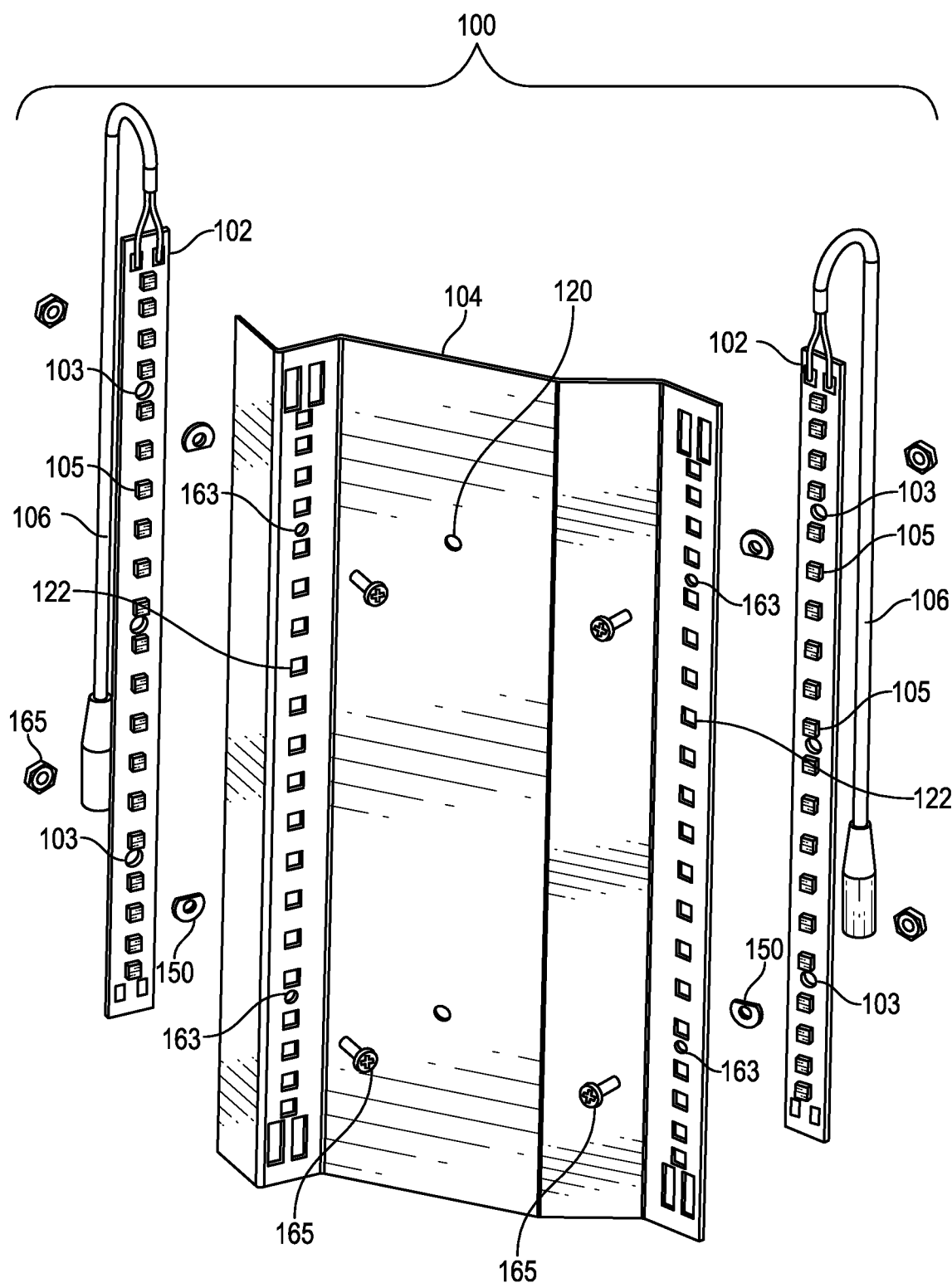
FIG. 4 is a front exploded view of the light kit assembly of the FIG. 1 embodiment in a dis-assembled configuration.
Figure 5:
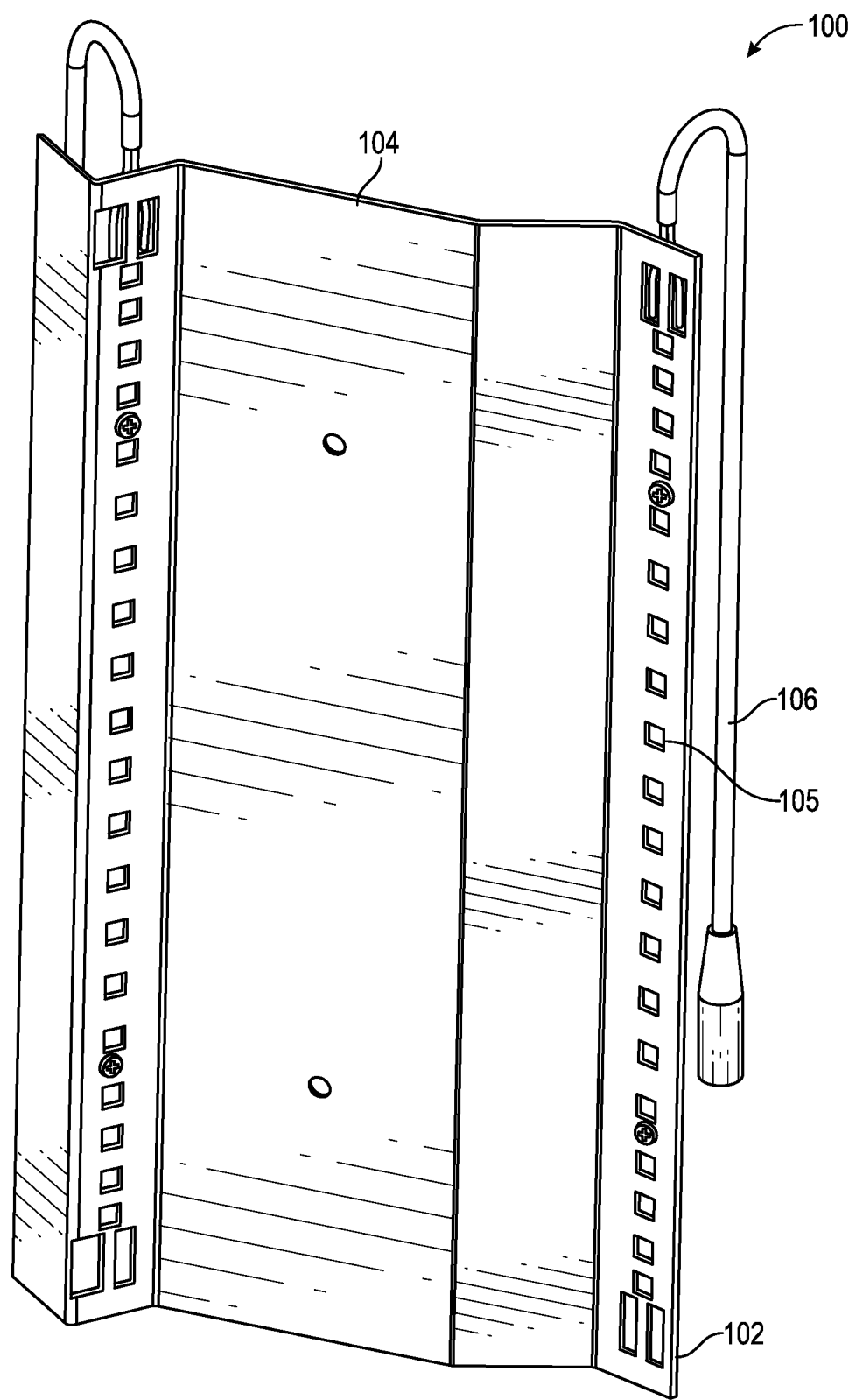
FIG. 5 is a front perspective view of the light kit assembly of the FIG. 4 embodiment in an assembled configuration.

Turning to FIGS. 4 and 5, is one embodiment of the light kit assembly 100. In the illustrated embodiment, the light kit assembly 100 includes two light sources 102 that are attached to a mounting plate 104. In other embodiments, the light kit assembly 100 can include one or more light sources 102.

Figure 6:
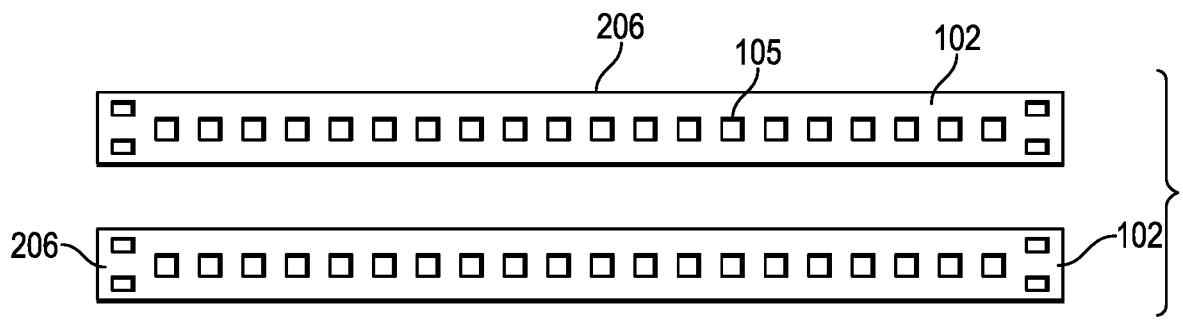
FIG. 6 is front view of two of light sources for use with the light kit assembly of the FIG. 1 embodiment.

In the illustrated embodiment, the light sources 102 include a plurality of ultraviolet-C "UVC" lamps 105 assembled into UVC LED strips 206 as shown in FIG. 6. In one form, the UVC LED strips 206 emit ultraviolet light having 275 nm wavelength and are approximately 210 mm long and 12 mm thick. UVC radiation is a disinfectant for air, water, and nonporous surfaces. Other configurations or types of UVC LED strips can be used in other embodiments of the light sources 102. UVC radiation reduces the spread of bacteria and viruses and are frequently known as "germicidal" lamps. The light sources 102 configured as UVC LED strips 206 may emit a broad range of UV wavelengths, and may also emit infrared or electromagnetic radiation. Other embodiments of the light sources 102 may include UV lamps 105, or alternatively and/or additionally, mercury lights, Xenon lights, and/or excimer lamps, to name a few examples. It is contemplated that other types of light or energy sources may be used to disinfect or sanitize the carrier and the carrier pocket 200 when assembled with the customer unit 202. The light sources 102 include a plurality of mounting holes 103 for assembly of the light sources 102 to the mounting plates 104 such that the mounting holes 103 align with a corresponding number of mounting holes 163 in the mounting plates 104 wherein a fastener or other connector is inserted through the mounting holes 103 and 163 to attach the light sources 102 to the mounting plates 104 as described in more detail below. The plurality of UVC lamps 105 are arranged and configured to align with a corresponding number of light holes in the mounting plates 104 to assemble the light sources 102 thereto such that the UVC lamps 105 of the light sources 102 emit light through the light holes in the mounting plates 104 as described in more detail below.

Figure 7:
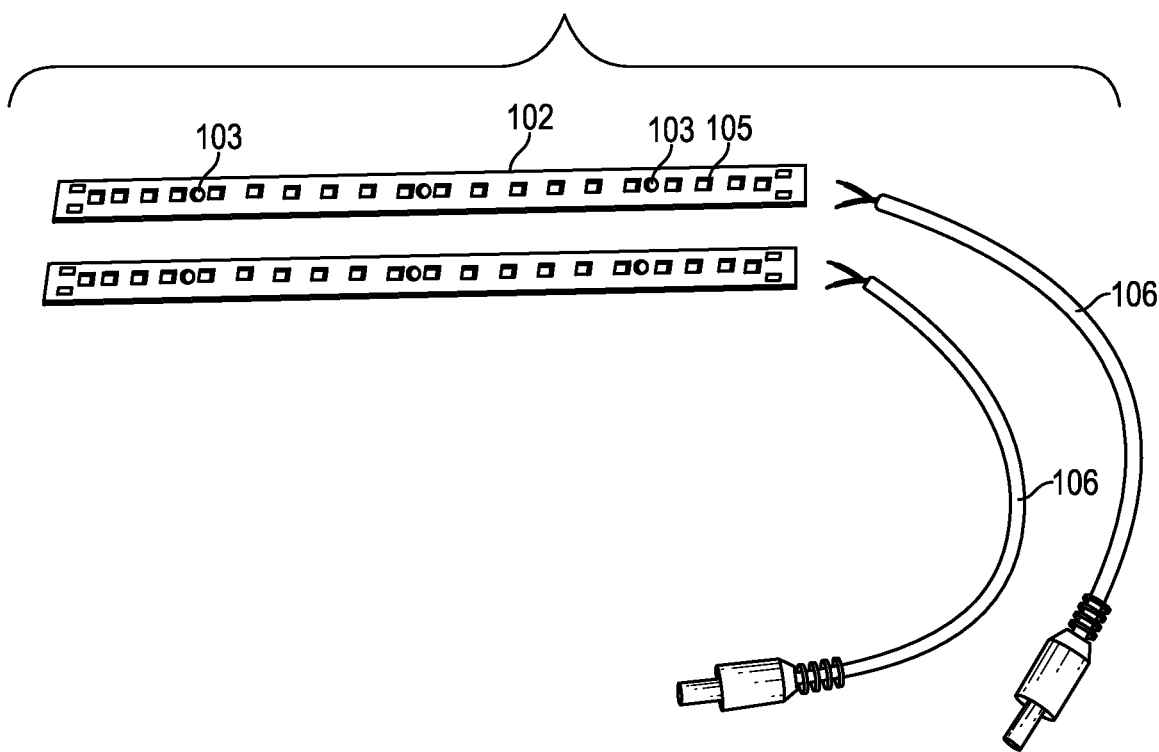
FIG. 7 is a front view of the two light sources of the FIG. 4 embodiment in a dis-assembled configuration.

Turning to FIG. 7, power cables 106 are illustrated that can be attached to the light sources 102. In one form, the power cables 106 are solder power cables 69-A1P attached to light sources 102. In other embodiments, the power cables 106 may be configured differently.

Figure 8:
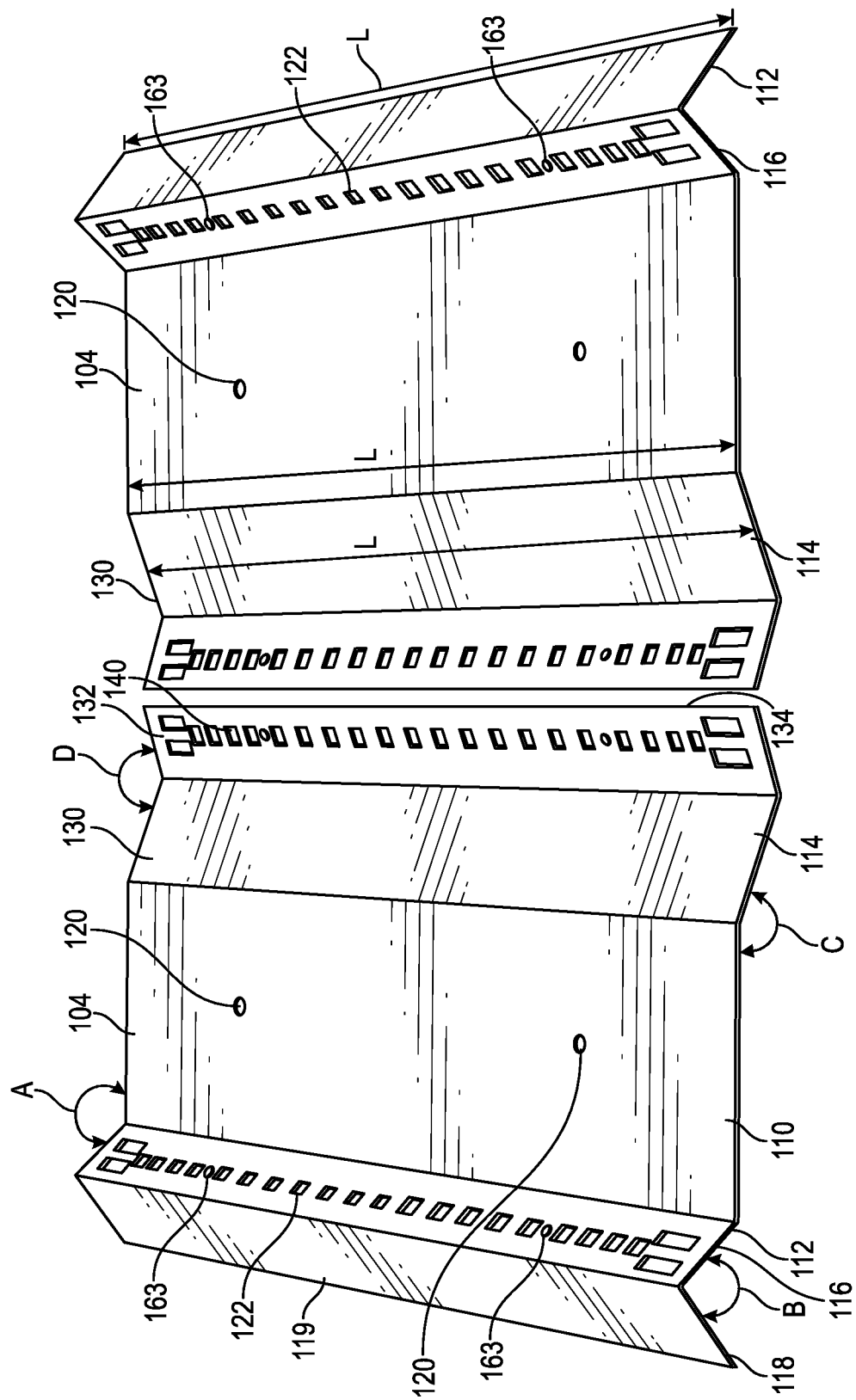
FIG. 8 is a front perspective view of the mounting plates of the FIG. 4 embodiment.

Turning to FIG. 8, the two mounting plates 104 are identical to each other therefore for the sake of brevity only one mounting plate 104 will be described. As illustrated, the first mounting plate 104 is rotated 180 degrees from the second mounting plate 104. In other embodiments, the mounting plates 104 maybe configured differently from each other. The mounting plates 104 can be made of any material, for example, stainless steel, metal, and/or plastic, that can be configured to receive the light sources 102. Each of the mounting plates 104 include a back wall 110 that extends between a first wing 112 and a second wing 114. Each of the back wall 110 and the first and second wings, 112 and 114, respectively, have a length, L, that approximately corresponds to or is longer than a length of the light sources 102. In other embodiments the length, L, of the back wall 110 may be longer or shorter than the length, L, of the first and second wings, 112 and 114. The back wall 110 includes two openings 120 sized to receive a fastener or an electric cord there through.

The first wing 112 has a bi-folded shape with a first portion 116 adjacent the back wall 110 and extending to a second portion 118 that includes a free edge 119. A first backwall angle A spans between the first portion 116 and the back wall 110. A first wing angle B spans between the first portion 116 and the second portion 118. The first portion 116 includes a plurality of light holes 122 sized to receive the UVC lamps 105 on the light source 102 therein to further assemble and/or mount the light source 102 to the first portion 116 such that one of the light holes 122 is assembled with one of the UVC lamps 105. The second portion 118 does not include any openings or light holes but may in other embodiments. For example, in an alternative embodiment, the second portion 118 may include a plurality of light holes that are sized to receive the UVC lamps 105 on the light source 102 therein to further assemble and/or mount the light source 102 to the second portion 118.

The second wing 114 has a bi-folded shape with a first portion 130 adjacent the back wall 110 and extending to a second portion 132 that includes a free edge 134. The first portion 130 does not include any openings or light holes but may in other embodiments. For example, in an alternative embodiment, the first portion 130 may include a plurality of light holes that are sized to receive the UVC lamps 105 on the light source 102 therein to further assemble and/or mount the light source 102 to the first portion 130. The second portion 132 includes a plurality of light holes 140 sized to receive the UVC lamps 105 on the light source 102 therein to further assemble and/or mount the light source 102 to the second portion 132. A second backwall angle C spans between the first portion 130 and the back wall 110. A second wing angle D spans between the first portion 130 and the second portion 132.

The unique folded shape of the mounting plate 104 and unique placement of two of the mounting plates 104 on opposite side panels of the carrier pocket 200, when the light kit assembly 100 is assembled with the carrier pocket 200, enable the light sources 102 to emit UV light to cover an area of approximately 360 degrees to sanitize all or substantially all of the exterior surface area of the carrier 204 and the air within the carrier pocket 200. This is beneficial because UV light does not penetrate through the exterior surface of the carrier 204 to the interior of the carrier 204. Therefore the unique placement of light sources 102 on the mounting plates 104 and the unique configuration of the mounting plates 104 emit wavelength around the outer surface of the carrier 204 that is highly effective to sanitize the outer or exterior surface area of the carrier 204 that an individual may touch or contact.

To assemble the light sources 102 with the mounting plates 104, the two mounting plates 104 are arranged on a surface in a mirrored position to each other as illustrated in FIG. 8. This arrangement is also beneficial for installation of the mounting plates 104 with the left and right panels of the carrier pocket 200 because the mirrored arrangement of the mounting plates 104 in the carrier pocket 200 enables more of the exterior surface area of the carrier 204 to be sanitized. In other embodiments, the mounting plates 104 are not positioned side by side and not in a mirrored arrangement in either the assembly of the light sources 102 with the mounting plates 104 or the installation of the mounting plates 104 with the carrier pocket 200.

Figure 9:
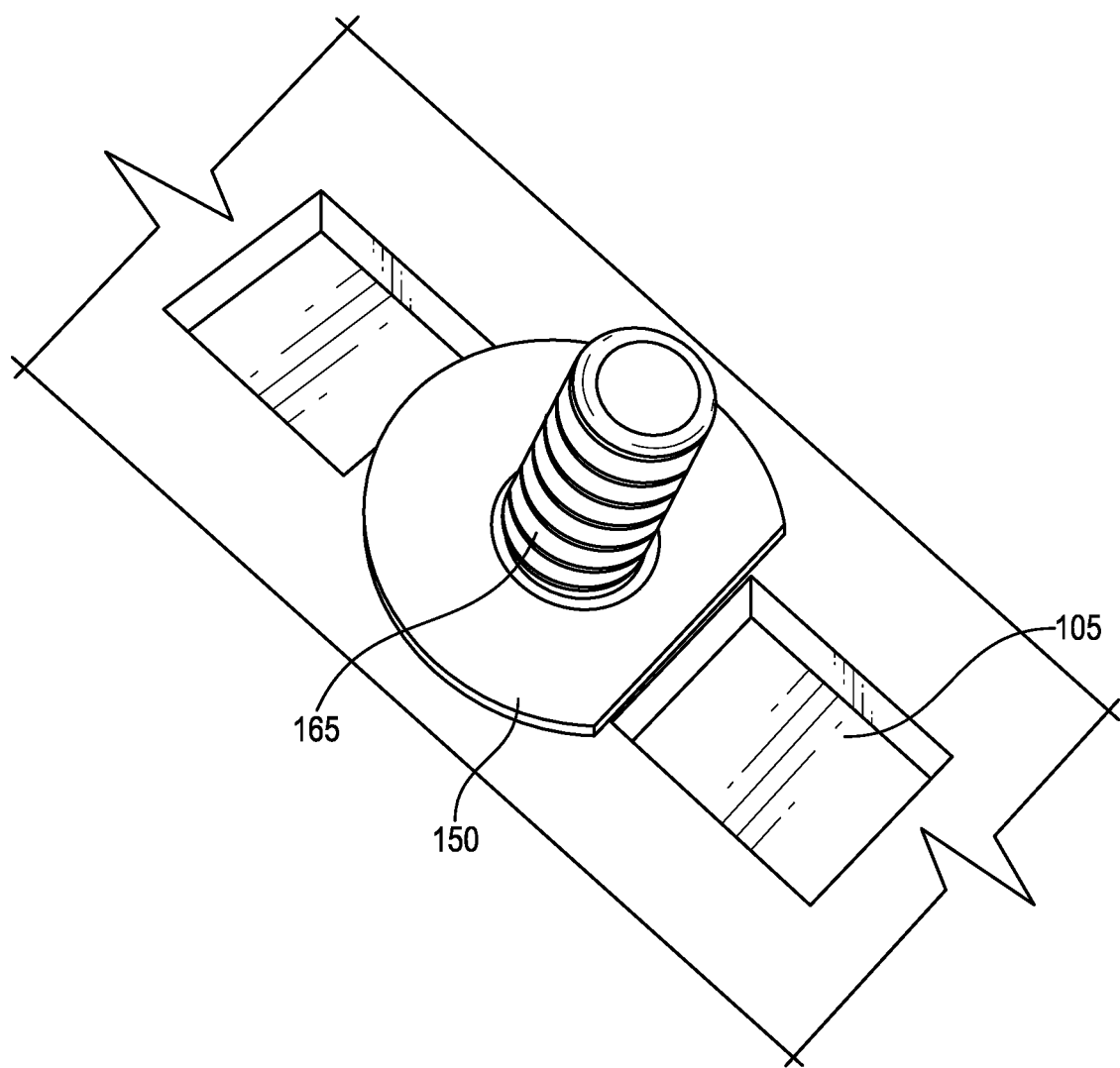
FIG. 9 is a partial perspective view of a fastener and washer of the FIG. 4 embodiment assembled with one of the light sources.
Figure 10:
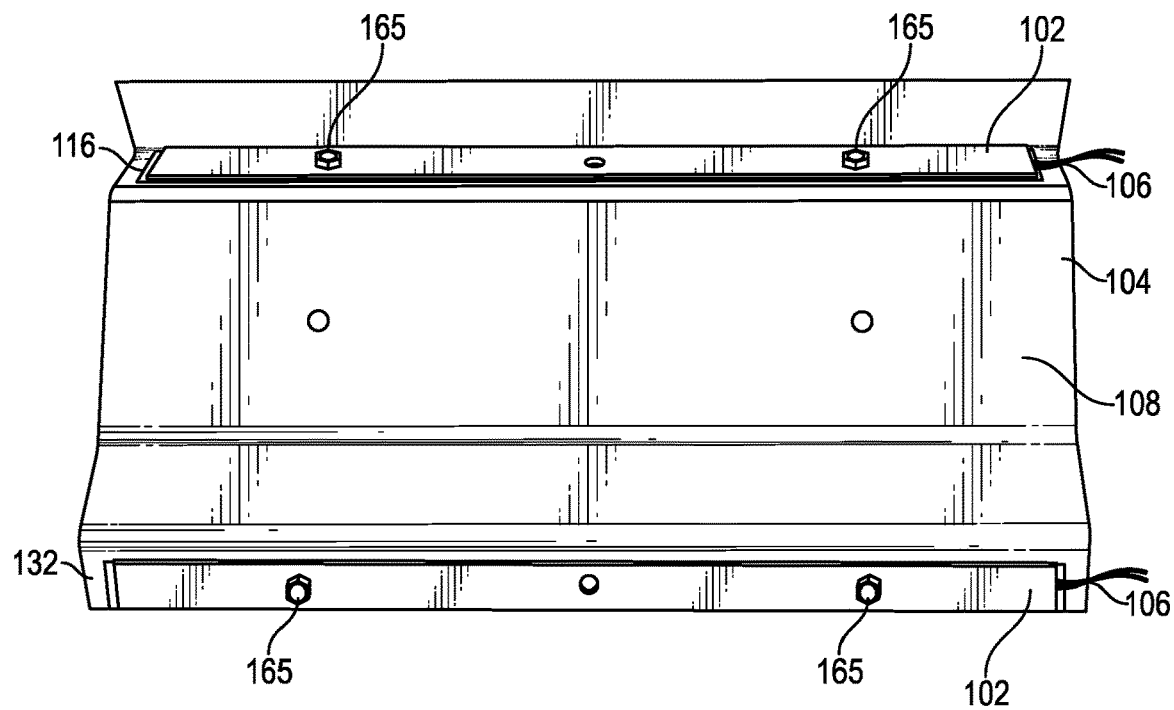
FIG. 10 is a rear view of the FIG. 5 embodiment.

The light sources 102 are assembled to a bottom surface 108 of the mounting plates 104 such that the power cables 106 extend from the bottom surface 108 as illustrated in FIG. 10. The light source 102 is positioned on the bottom surface 108 of the mounting plate 104 such that each of the UVC lamps 105 aligns with one of the plurality of light holes 122 of the first portion 116. Similarly, a second light source 102 is positioned on the bottom surface 108 of the mounting plate 104 such that each of the UVC lamps 105 aligns with one of the plurality of light holes 140 of the second portion 132. In particular, the light sources 102 are mounted with a trimmed nylon washer 150 between the light source 102 and the mounting plate 104 using one of a plurality of fasteners 165 such as, screws and lock nuts, through each of the mounting holes 103 and 163 to attach the light sources 102 to the mounting plates 104. In one embodiment, four round nylon washers 150 are trimmed with a knife, side cutters, or other cutting means, to remove a portion of an edge of the round nylon washers 150. Illustrated in FIG. 9 is the trimmed nylon washer 150 that is assembled with the fastener 165.

Figure 11:
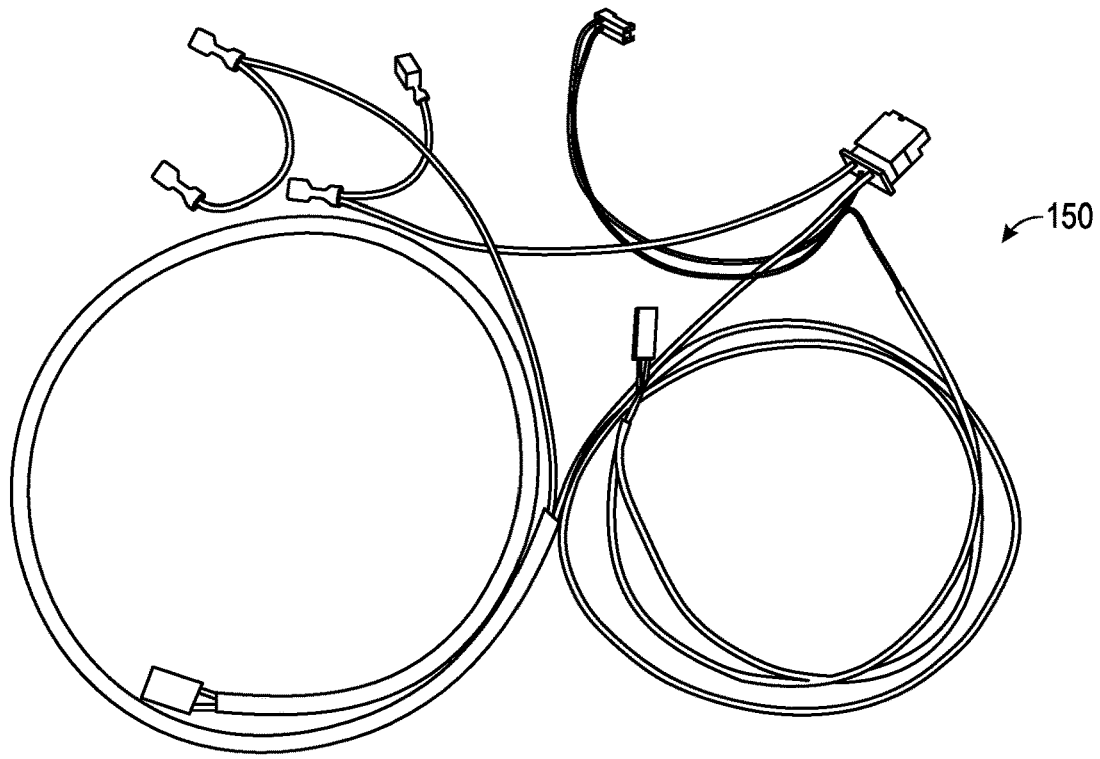
FIG. 11 is a front view of one embodiment of a wire harness input that can be assembled with the FIG. 1 embodiment.
Figure 13:
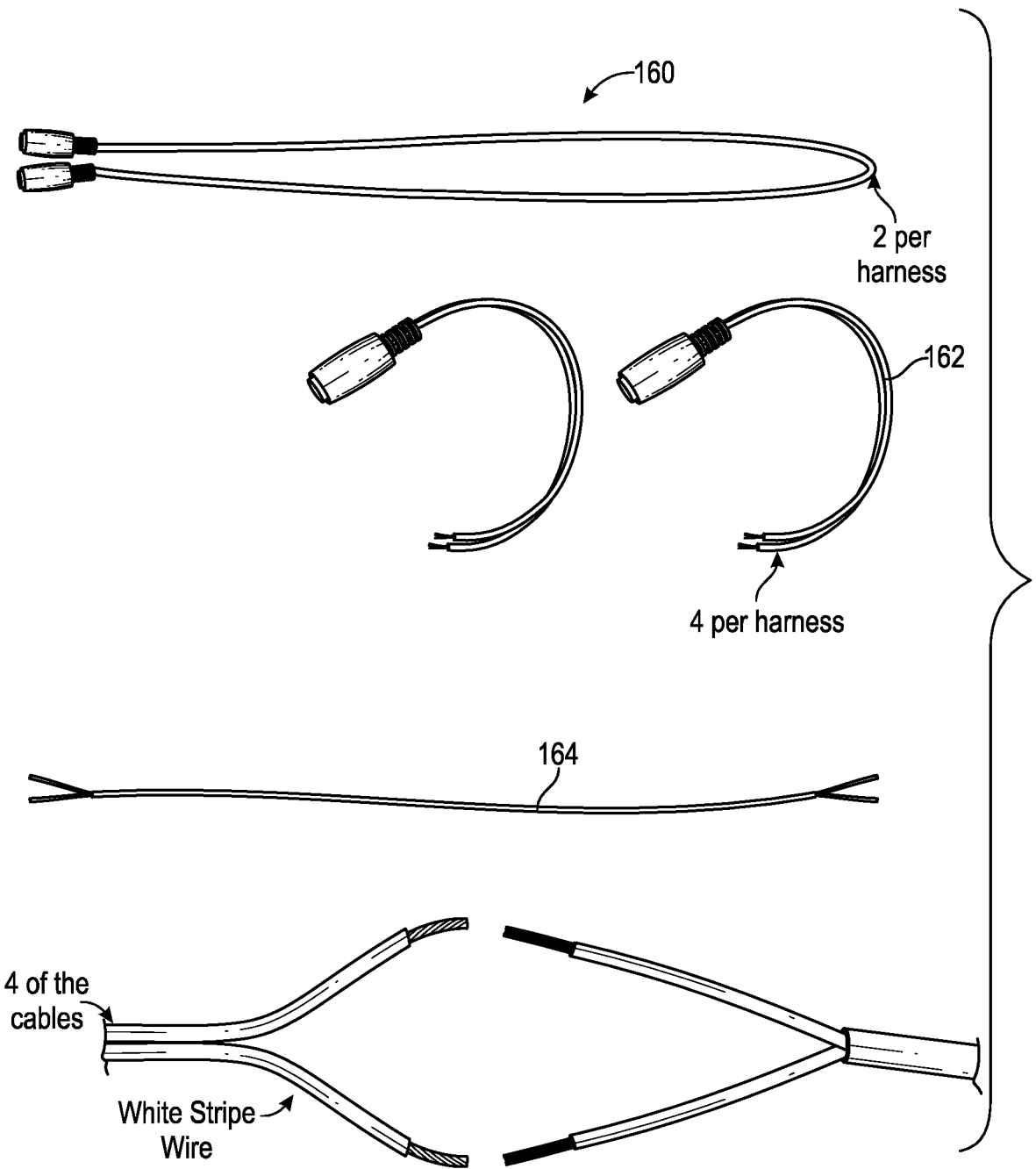
FIGS. 13 and 14 are front views of one embodiment of a wire harness output that can be assembled with the FIG. 1 embodiment.

FIGS. 11 and 12 illustrate an embodiment of a wire harness input 150 that is configured for assembly with the light kit assembly 100. In other embodiments, the wire harness input 150 is configured differently.

Figure 14:
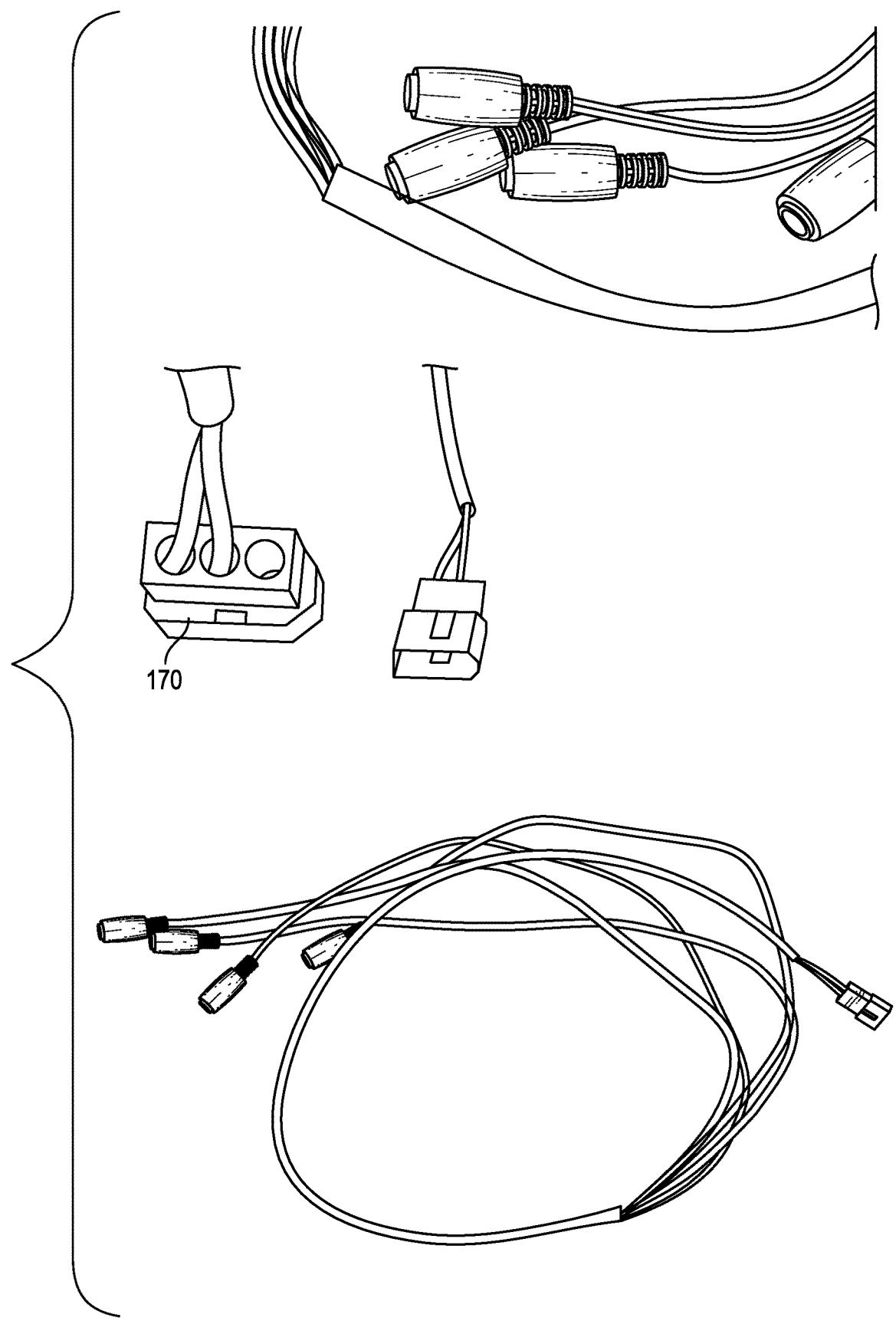

FIGS. 14 and 15 illustrate an embodiment of a wire harness output 160 that is configured for assembly with the light kit assembly 100. In other embodiments, the wire harness output 160 is configured differently. The wire harness output 160 is cut in half to create two cable assemblies 162 wherein the wire conductors of the cable assemblies 162 are split and the ends are stripped approximately ⅜". The wire harness output 160 includes a conductor cable 164 having a length of approximately 18 inches wherein approximately 1½" of casing is removed from both ends of the conductor cable 164. The wires on one end of the conductor cable 164 are stripped approximately ⅜" and the wires on the other end of the conductor cable 164 are stripped approximately ⅛". Next, the four half cable assemblies 162 are soldered to the two conductor cables 164 and wire the white stripe to red. A first shrink tube (not illustrated) is placed over the red/white stripe connection, then a second shrink tube is placed over both connections. There will be four of these cables. An AMP socket is installed on both of the red and black wires of the cables. Next as illustrated in FIG. 14, an AMP 3-position female connector 170 is installed on the cables such that the red wire is in position #2 and the black wire is in position #3. The #1 position is left empty in the AMP 3-position female connector 170.

Figure 15A:
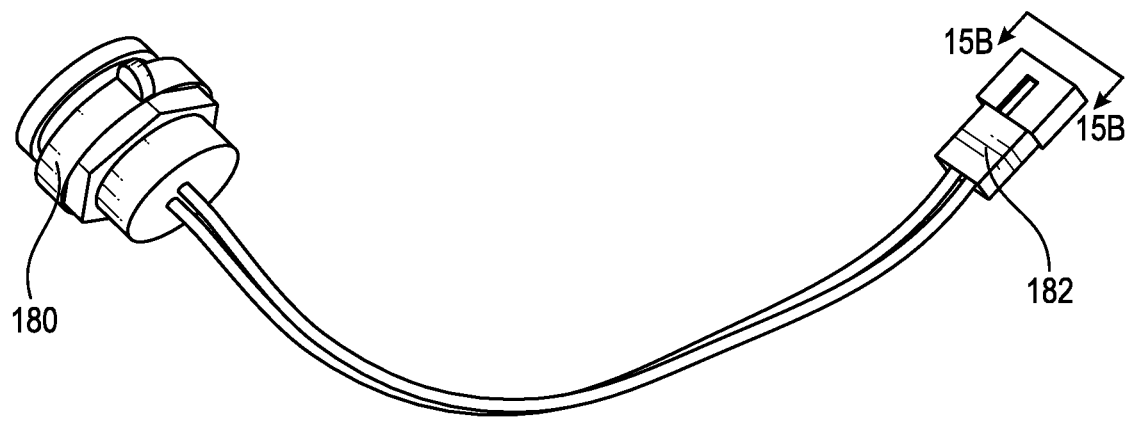
FIG. 15a is side view of a colored indicator light of the FIG. 1 embodiment.
Figure 15B:
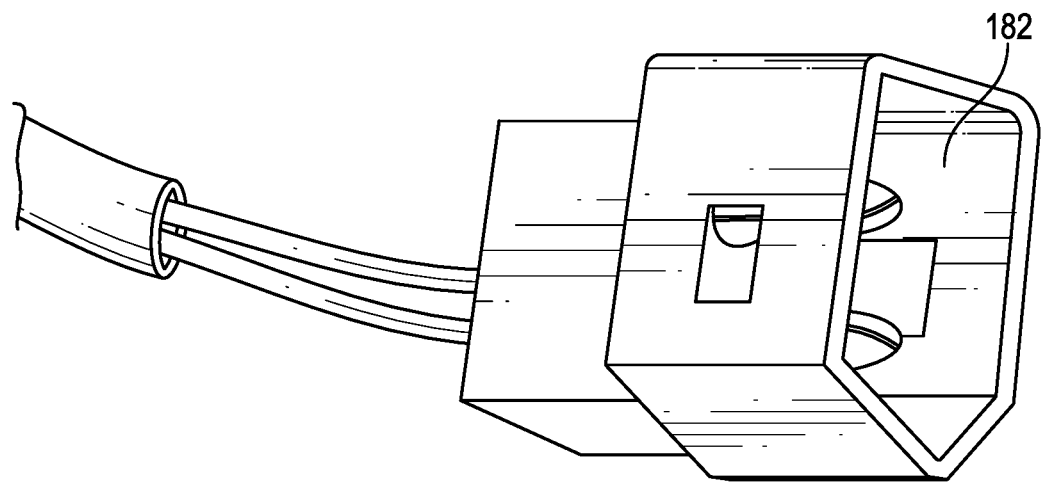
FIG. 15b is an end view of the colored indicator light of the FIG. 15a embodiment.
Figure 16:
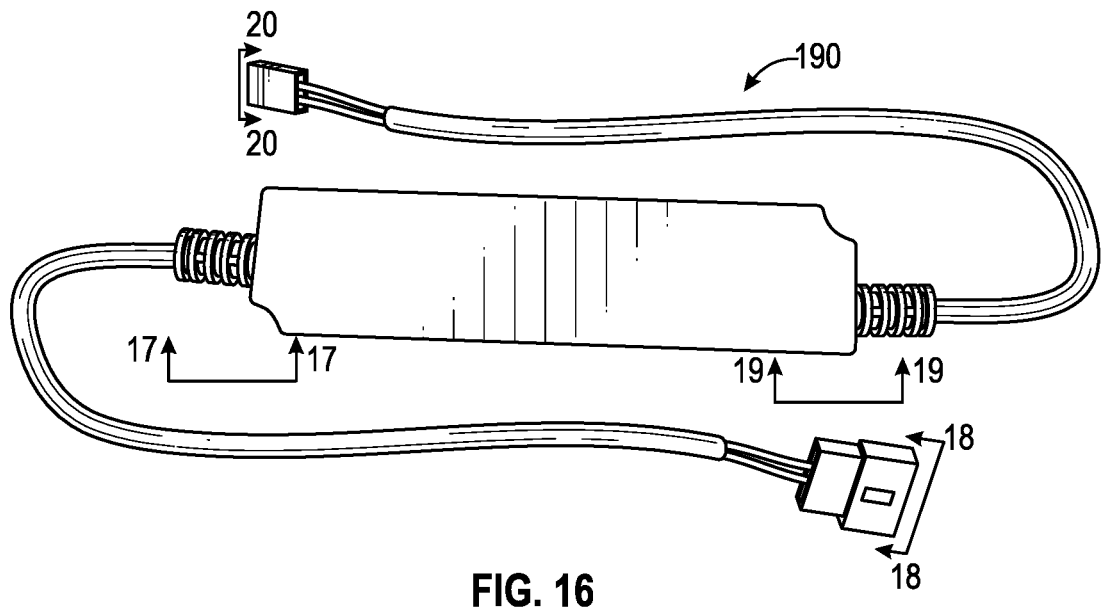
FIGS. 16-21 are front views of a power supply assembly of the FIG. 1 embodiment.
Figure 17:
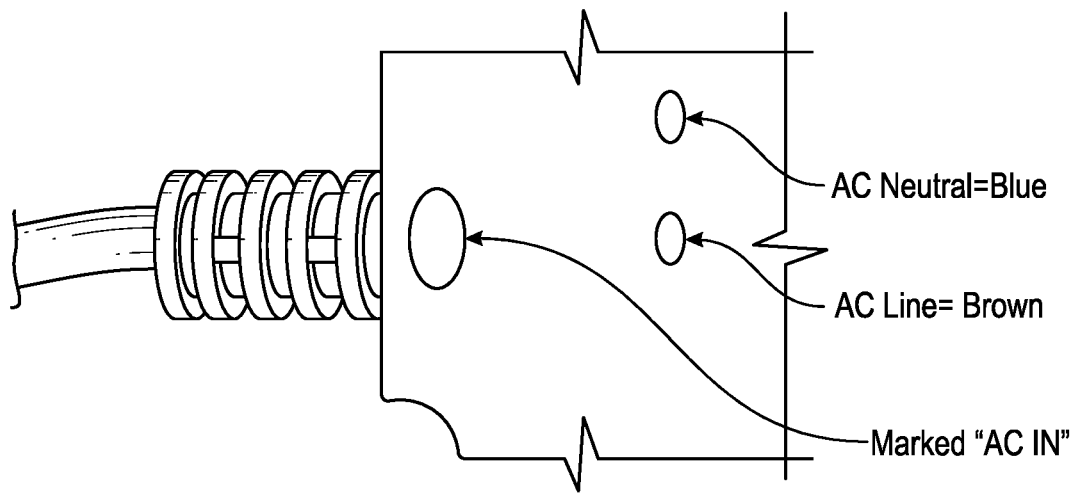
Figure 18:
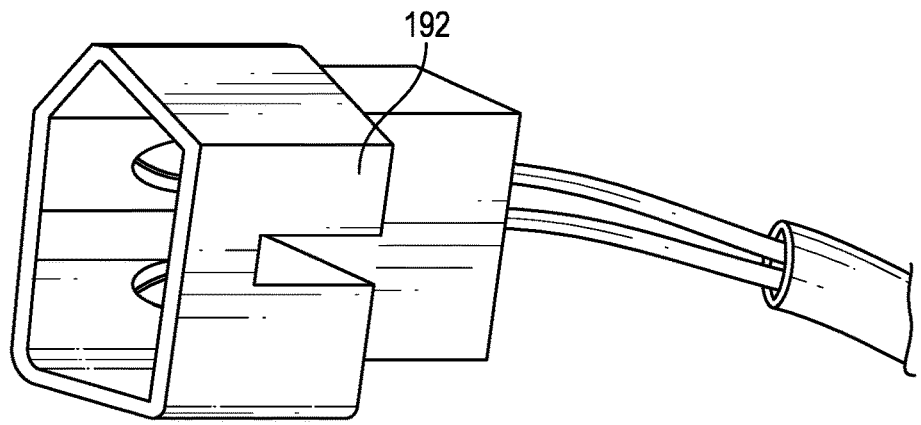
Figure 19:
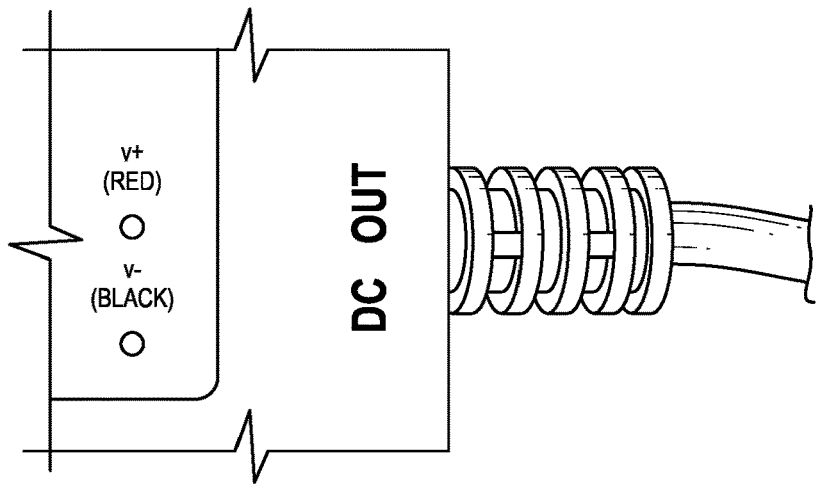
Figure 20:
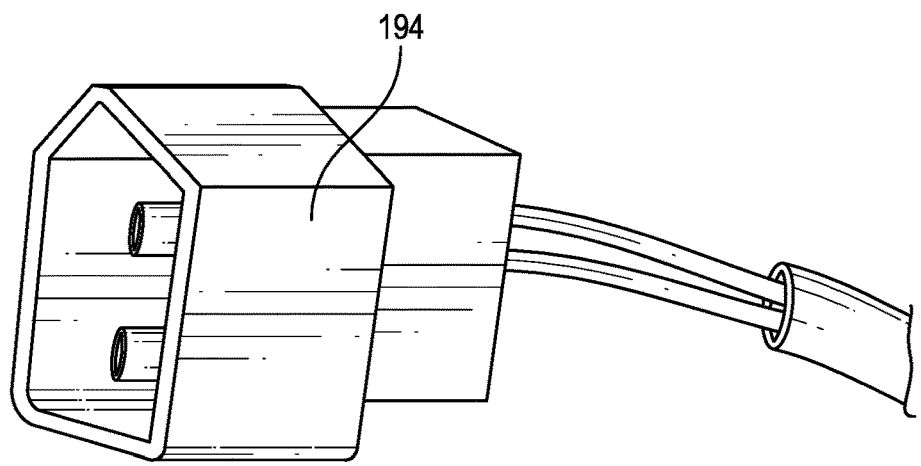

FIGS. 15a and 15b illustrate an optional colored indicator light 180 that is configured for assembly with the light kit assembly 100. In one form, the indicator light 180 is a blue LED light however in other embodiments the indicator light 180 may be a different color. The indicator light 180 includes AMP pins to both wires and an AMP 2-position female connector 182 that is attached or connected to both wires. The red wire is located in position #1 and the black wire is located in position #2 of the female connector 182.

Figure 21:
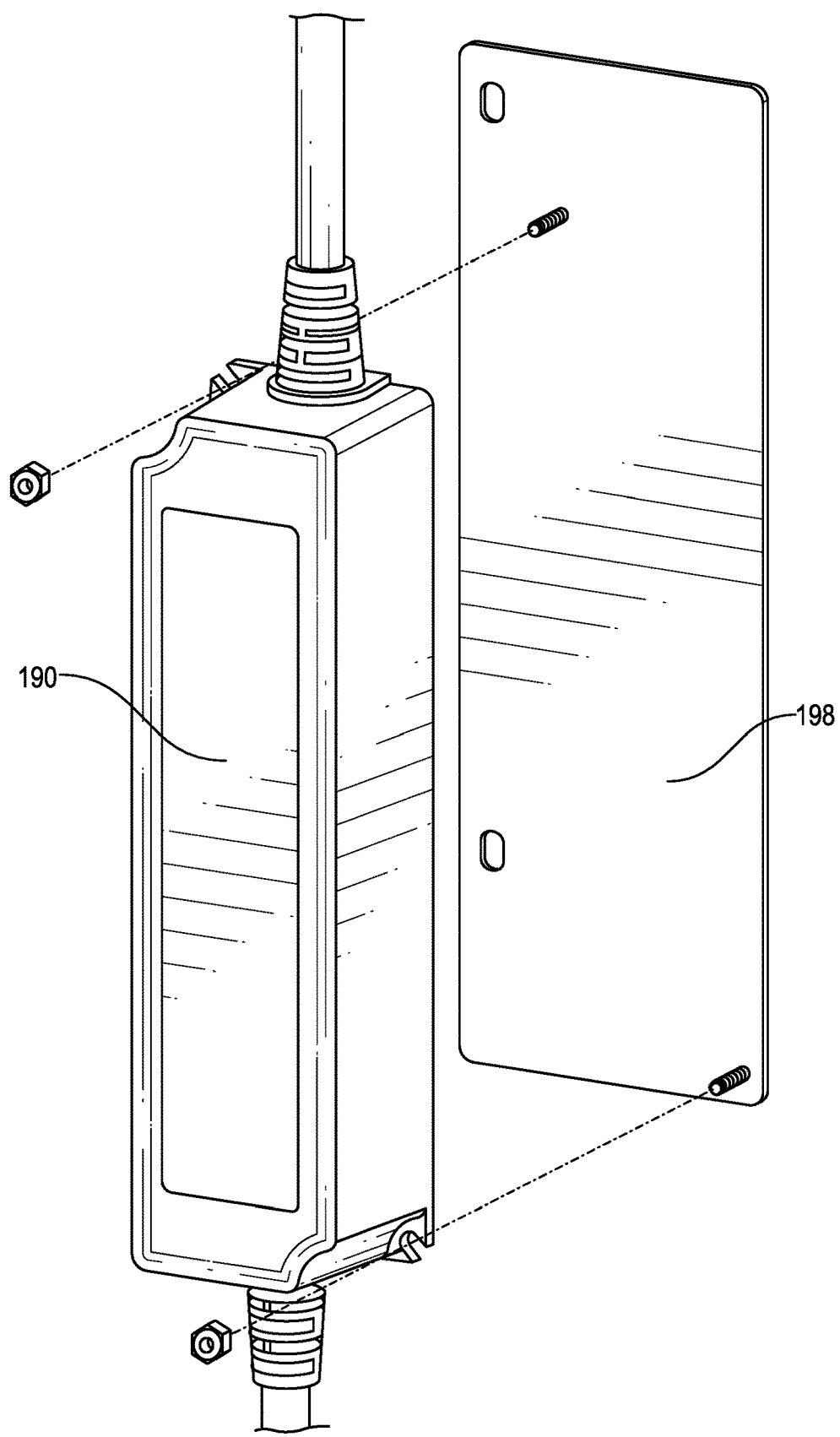
Figure 22:
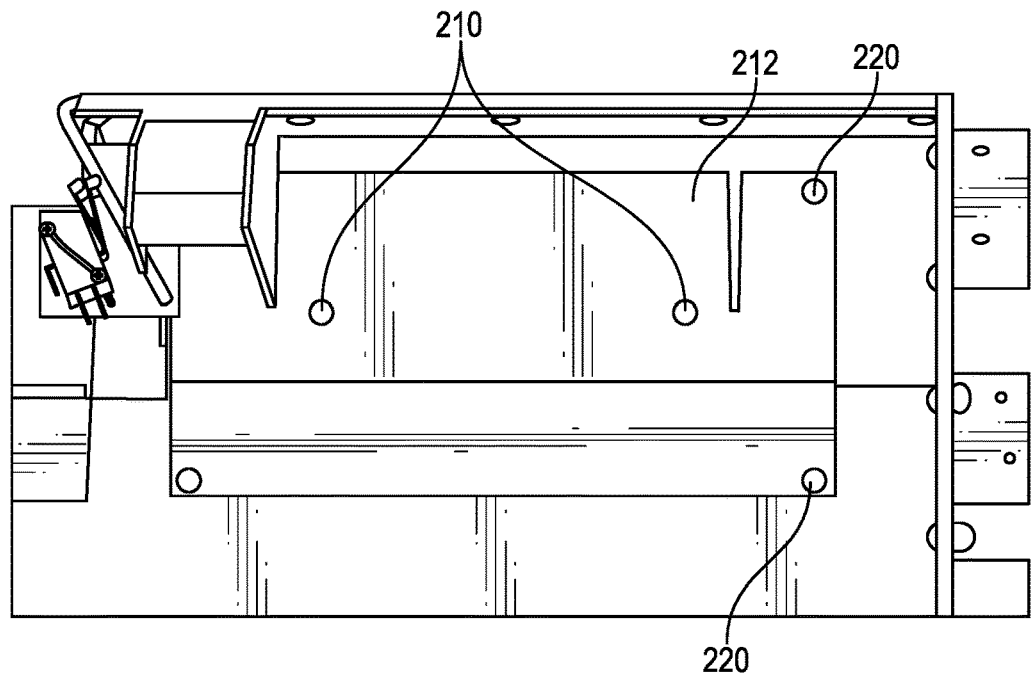
FIG. 22 is a front view of a panel of the carrier pocket of the customer unit.
Figure 23:
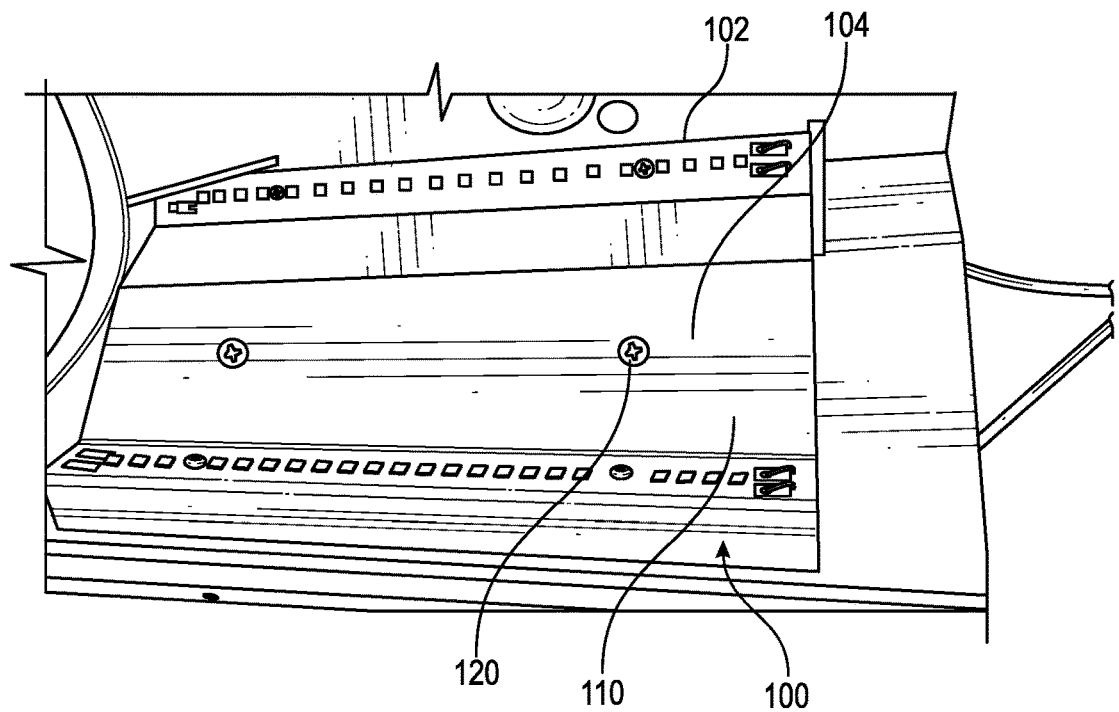
FIG. 23 is a front view of the light kit assembly attached to the panel of the carrier pocket of the customer unit of the FIG. 22 embodiment.
Figure 24:
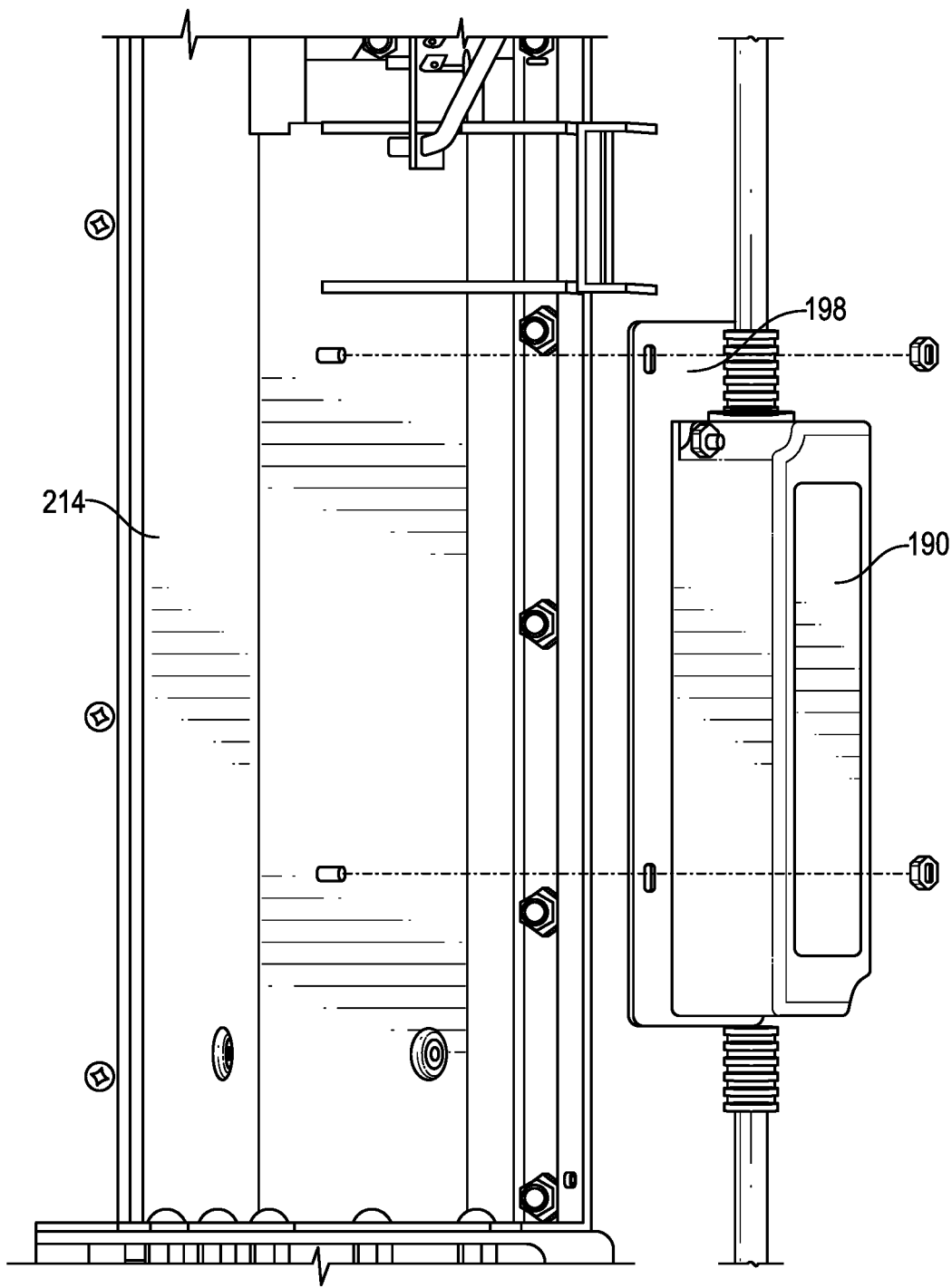
FIG. 24 is a front view of a power supply assembly for assembly to an outside face of the panel of the carrier pocket of the customer unit of the FIG. 22 embodiment.

FIGS. 16-20 illustrate a power supply assembly 190 for the light kit assembly 100. In other embodiments, the power supply assembly 190 is configured differently. The power supply assembly 190 includes a power input connection and AMP pins installed to both the blue and brown wires. An AMP 3-position female connector 192 is installed such that the brown wire is placed in position #1, the blue wire is placed in position #3, and the #2 position is left empty. The power supply assembly 190 includes an output power connection. The power supply assembly 190 includes an AMP socket connected to both the red and black wires. An AMP 3-position male connector 194 is connected to the red wire in position #2, the black wire in position #3, and the #1 position is left empty. Illustrated in FIG. 21 is the power supply assembly 190 that is mounted to a mounting plate 198 as shown using a plurality of fasteners such as screws and lock nuts.

Figure 25:
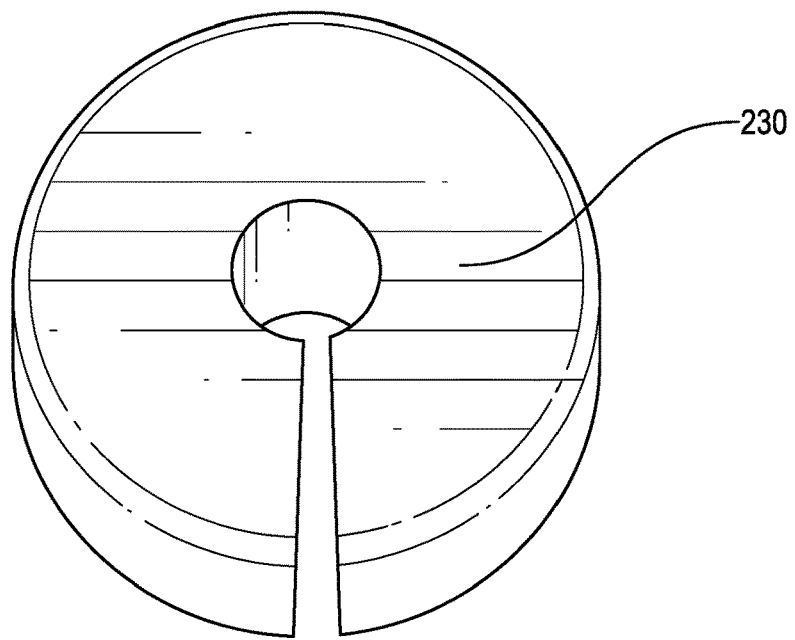
FIG. 25 is a front view of a split grommet.
Figure 26:
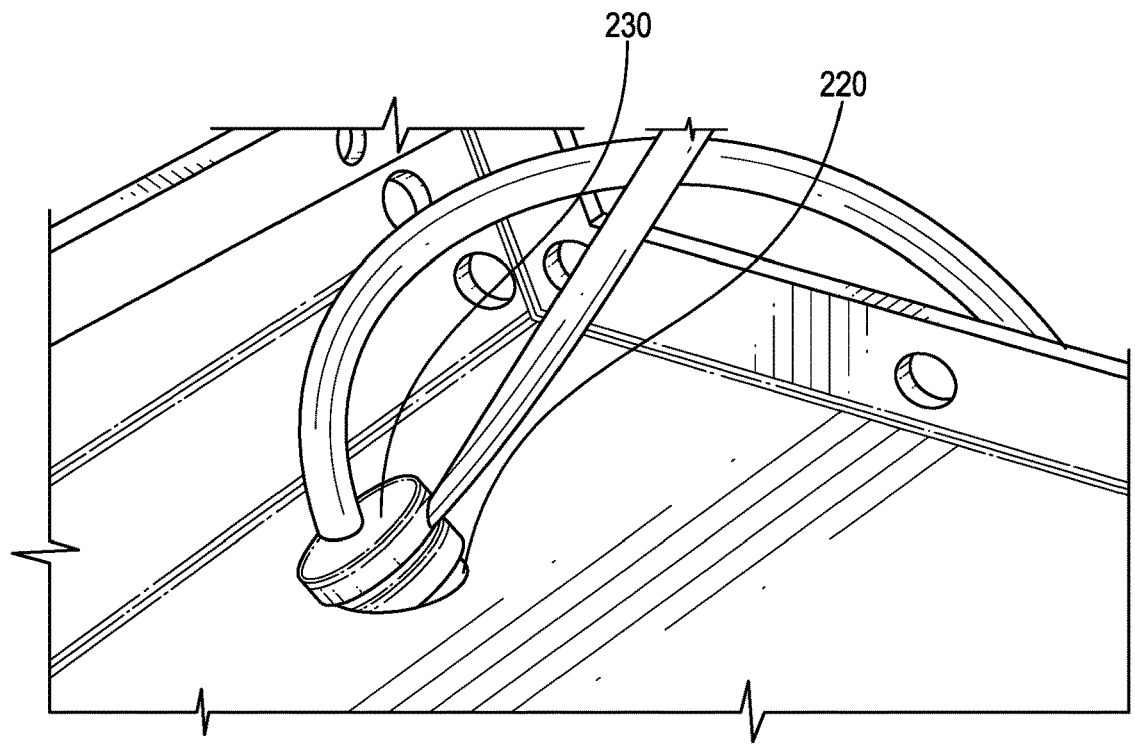
FIG. 26 is a front view of the split grommet of FIG. 25 positioned into a wire access hole of the FIG. 22 embodiment.

FIGS. 22-26 illustrate the light kit assembly 100 that is mounted to the carrier pocket 200 of the customer unit 202. Two of the light kit assemblies 100 are mounted to the carrier pocket 200, a first one on the left side panel 212 and a second one on a right side panel (not illustrated) of the carrier pocket 200. For the sake of brevity, the attachment of the light kit assembly 100 to a left side panel 212 of the carrier pocket 200 will be described next however the attachment of the light kit assembly 100 to the right side panel of the carrier pocket 200 will be similar. Two mounting plate holes 210 are formed in the left side panel 212 of the carrier pocket 200 of the customer unit 202. The mounting plate holes 210 are sized and positioned to align with the openings 120 in the back wall 110 of the mounting plate 104 when the mounting plate 104 is assembled with the left side panel 212. Two wire access holes 220 are formed in each of the side panels 212 for positioning the power cables 106 through the wire access holes 220 in the left side panel 212. The mounting plate 104 is secured or attached to the left side panel 212 with a fastener, screw, bolt, washer, and/or lock nuts through the mounting plate holes 210 and the openings 120. The power supply assembly 190 is attached to an outside face 214 of the left side panel 212 which is outside of the pocket 200 with a fastener or other means to hold the mounting plate 190 thereon. This process is repeated to mount the second of the light kit assemblies 100 to the right side panel of the carrier pocket 200. In the illustrated embodiment, there is only one of the power supply assembly 190 mounted to the left side panel 212 however in other embodiments there may be a second of the power supply assembly 190 mounted to the right side panel. Optionally as illustrated in FIGS. 25 and 26, a split grommet 230 is positioned over each over each LED wire and positioned into the wire access holes 220.

Figure 27:
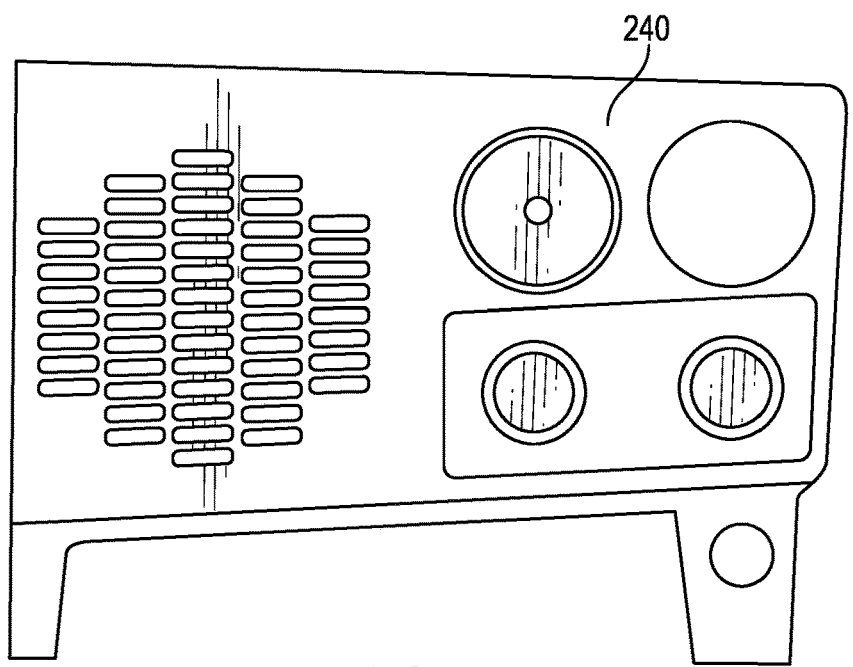
FIG. 27 is a front view of an optional indicator light assembled with the customer unit.
Figure 28:
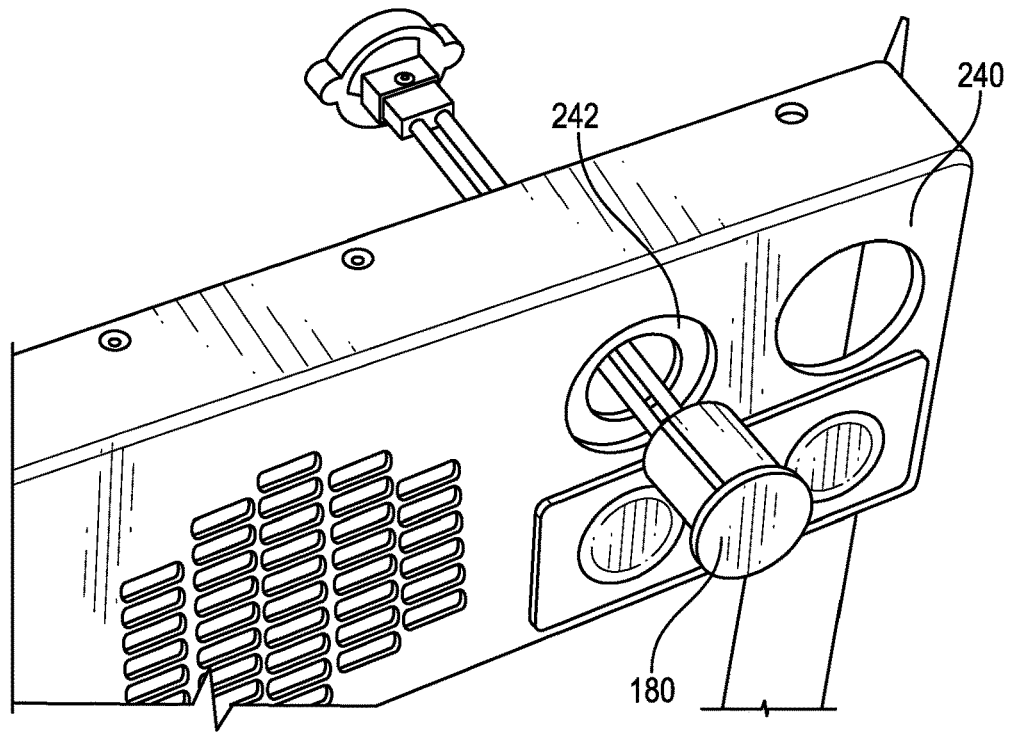
FIG. 28 is a front view of the optional indicator light of FIG. 27 being assembled with the customer unit.
Figure 29:
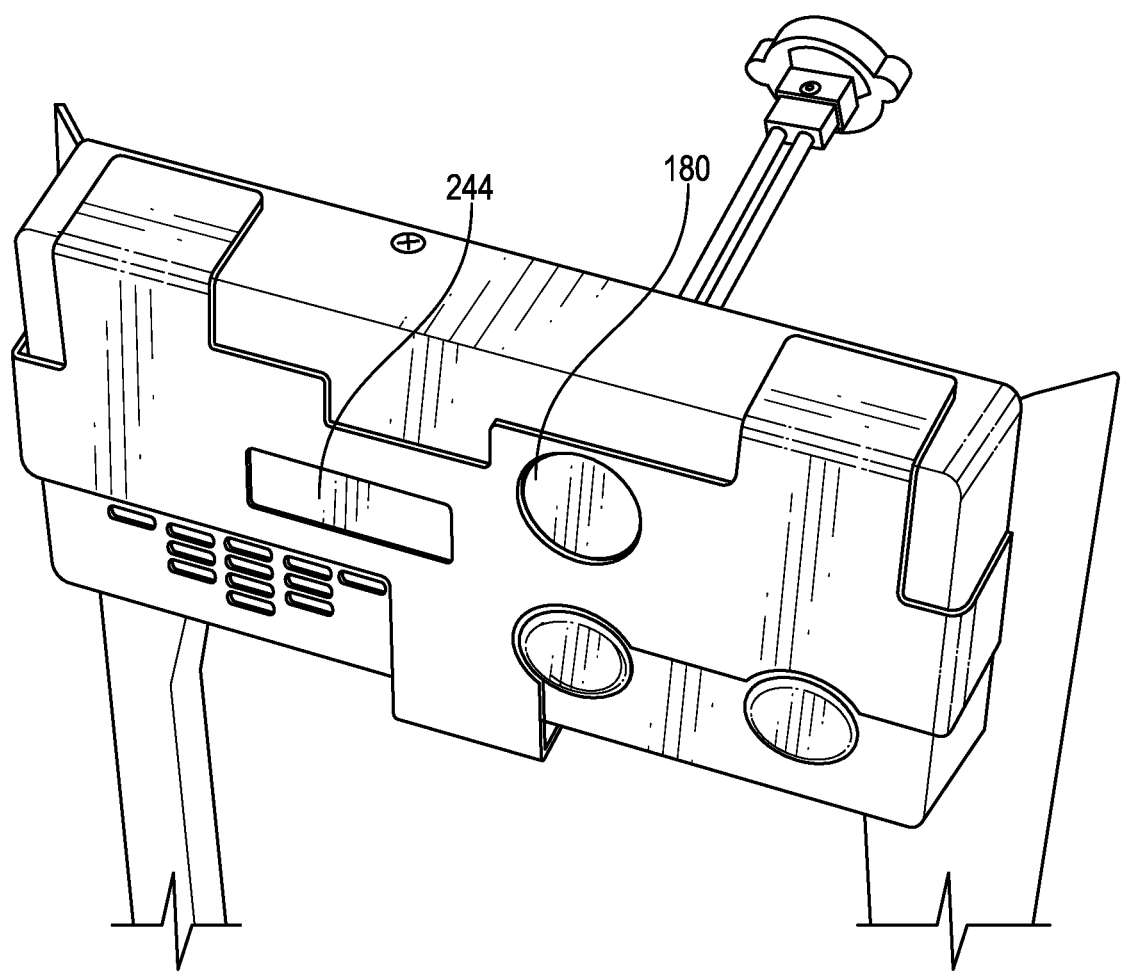
FIG. 29 is a front view of the optional indicator light of FIG. 27 being assembled with the customer unit.

FIGS. 27-29 illustrate the indicator light 180 assembled into an opening 242 in a fascia 240 of the customer unit 202. Optionally, a "Sanitizing" label 244 is attached to the fascia 240. Beneficially, the indicator light 180 alerts a user that the sanitization process of the carrier is being carried out.

Figure 30:
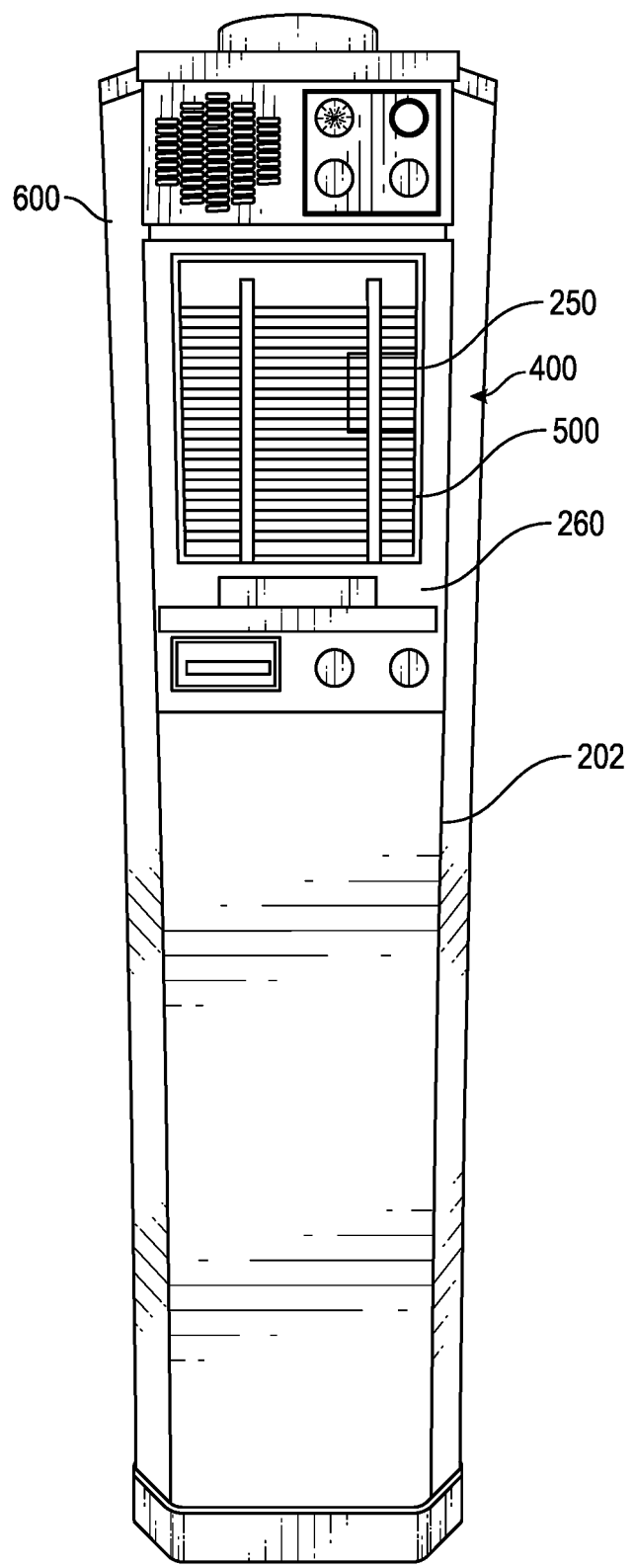
FIG. 30 is a front view of a second embodiment of a light kit assembly assembled with a replacement carrier pocket.
Figure 31:
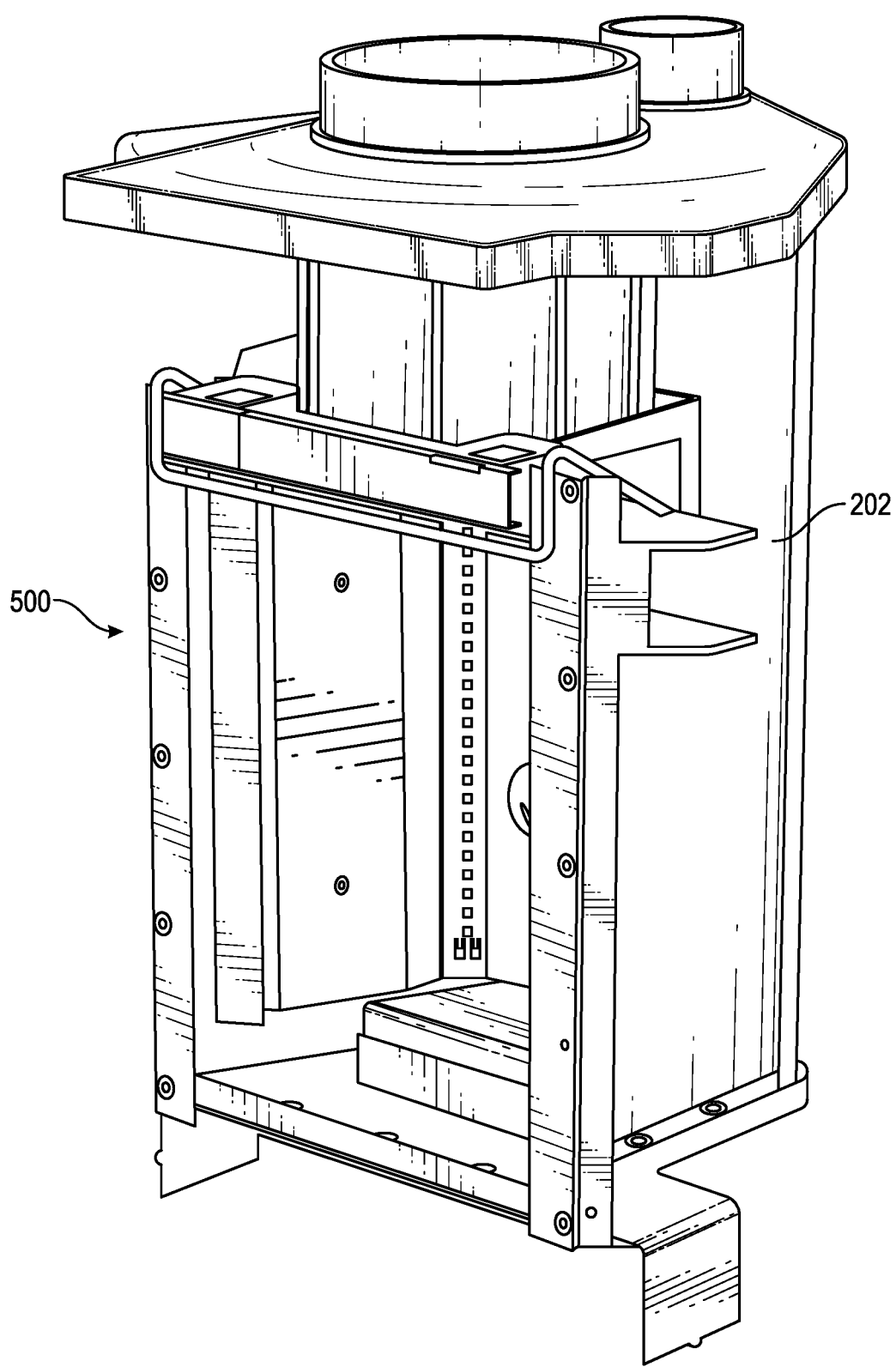
FIG. 31 is a partial perspective view of the light kit assembly assembled with the replacement carrier pocket installed in the customer unit of the FIG. 30 embodiment.

FIG. 30 illustrates a second embodiment of a light kit assembly 400 assembled with a replacement carrier pocket 260 to form a light kit subassembly 500. The light kit subassembly 500 is then installed in a customer unit 202 after removing the existing carrier pocket 200 of the customer unit 202. Also illustrated is the customer unit 202 including a customer unit door 250 in a closed position. The light kit assembly 400 is similar to the light kit assembly 100. As such, the light kit assembly 400 includes one or more light sources 102 that are attached to the mounting plate 104. Illustrated in FIG. 31 is the light kit subassembly 500 installed in the customer unit 202 using one or more fasteners, wherein the customer unit door 250 is removed for clarity.

IOT/Connectivity Features

In certain embodiments, the light kit assembly 100 is coupled to a controller 600 structured to perform certain operations to control operation of the light source 102, and optionally one or more of the customer unit 202, the teller unit 302, and the carrier 204. In other embodiments, the light kit assembly 400 is coupled to the controller 600. In certain embodiments, the controller 600 forms a portion of a processing subsystem including one or more computing devices having memory, processing, and communication hardware. The controller 600 may be a single device or a distributed device, and the functions of the controller 600 may be performed by hardware or by instructions encoded on computer readable medium. The controller 600 may be included within, partially included within, or completely separated from a teller unit controller or a customer unit controller (not shown). The controller 600 is in communication with any sensor or actuator throughout the light kit assembly 100 or 400, including through direct communication, communication over a datalink, and/or through communication with other controllers or portions of the processing subsystem that provide sensor and/or actuator information to the controller.

In certain embodiments, the controller 600 is described as functionally executing certain operations. The descriptions herein including the controller operations emphasizes the structural independence of the controller 600, and illustrates one grouping of operations and responsibilities of the controller 600. Other groupings that execute similar overall operations are understood within the scope of the present application. Aspects of the controller 600 may be implemented in hardware and/or by a computer executing instructions stored in non-transient memory on one or more computer readable media, and the controller 600 may be distributed across various hardware or computer based components.

Example and non-limiting controller implementation elements include sensors providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), and/or digital control elements.

The listing herein of specific implementation elements is not limiting, and any implementation element for any controller described herein that would be understood by one of skill in the art is contemplated herein. The controllers herein, once the operations are described, are capable of numerous hardware and/or computer based implementations, many of the specific implementations of which involve mechanical steps for one of skill in the art having the benefit of the disclosures herein and the understanding of the operations of the controllers provided by the present disclosure.

One of skill in the art, having the benefit of the disclosures herein, will recognize that the controllers, control systems and control methods disclosed herein are structured to perform operations that improve various technologies and provide improvements in various technological fields. Without limitation, example and non-limiting technology improvements include improvements in light operation, sanitization of the outer surface of the carrier, and sanitization of the carrier pocket of the customer unit.

Certain operations described herein include operations to interpret or determine one or more parameters. Interpreting and determining, as utilized herein, includes receiving values by any method known in the art, including at least receiving values from a datalink or network communication, receiving an electronic signal (e.g. a voltage, frequency, current, or PWM signal) indicative of the value, receiving a software parameter indicative of the value, reading the value from a memory location on a non-transient computer readable storage medium, receiving the value as a run-time parameter by any means known in the art, and/or by receiving a value by which the interpreted or determined parameter can be calculated, and/or by referencing a default value that is interpreted or determined to be the parameter value.

Certain systems are described following, and include examples of controller operations in various contexts of the present disclosure. The controller 600 is operable to sanitize the carrier 204 in a drive-through banking system. The controller 600 is operable to position the carrier 204 in either the customer station or the teller station of the drive-through banking system. The controller 600 is operable to close a door of either the customer station 202 or the teller station 302 that contains the carrier 204 therein. The controller 600 is operable to operate the light kit assembly 100 or 400 that contains one or more UV light sources 102 mounted on the mounting plate 104 in either the customer station 202 or the teller station 302 that contains the carrier 204, wherein the UV light from the one or more UV light sources 102 is directed towards the carrier 204 for a designated sanitization period.

Operation of the light kit assemblies 100 and 400 will now be described. For the sake of brevity, only the operation of light kit assembly 100 is described, however the operation of the light kit assembly 400 is substantially the same. The controller 600 controls the operation of the light kit assemblies 100 and 400. The light function or operation of the light kit assembly 100 can be enabled or disabled manually by a technician and/or automatically by the controller 600. When the light function is disabled, the drive-through banking system including the customer unit 202, teller unit 302, and the carrier 204 will operate without operation of the light kit assembly 100. In a disabled mode of operation, the light sources 102 are non-operational. Alternatively, in an enabled mode of operation, the light sources 102 are operational. To recall the carrier 204 to the customer unit 202, the carrier recall button on the customer unit 202 is engaged.

In a normal mode of operation, the controller 600 operates the light source 102 to turn OFF and the customer and/or bankers can use the drive-through banking system including the customer unit 202, teller unit 302, and the carrier 204. The indicator light 180, if present, is also turned OFF by the controller 600 to indicate that no sanitization is occurring.

The light kit assembly 100 is operable in either an automatic sanitization mode of operation or a manual sanitization mode of operation. The light kit assembly 100 being operable in an automatic sanitization mode of operation by the controller 600 will now be described. After a period of time of inactivity of the customer unit 202, the customer door of the customer unit 202 will automatically close. In one form, the period of time of inactivity is approximately three (3) minutes however in other forms the amount of time may be longer or shorter. Alternatively, after a designated number of uses of the customer unit 202 by customers, the customer door will automatically close and the automatic sanitization mode of operation will take place. Some examples of the designated number of uses are 1, 5, or 10 uses after which the automatic sanitization mode of operation takes place. Either before or after the customer door closes, the carrier 204 is recalled to the carrier pocket 200 of the customer unit 202. After the customer door closes and the carrier is located in the carrier pocket 200, the light sources 102 are turned ON for a designated sanitization period. The indicator light 180 is also turned ON for the designated sanitization period. In one form, the designated sanitization period is three (3) minutes however the designated sanitization period may be longer or shorter. After the designated sanitization period has passed, the light sources 102 and the indicator light 180, if present, will automatically turn off and the customer door will remain closed until engagement from a customer or a banker with the customer unit 202 or the teller unit 302. Beneficially, a short duration for the designated sanitization period is helpful to manage customers' expectations for quick service.

During the automatic sanitization mode of operation, the light function of the light sources 102 and the indicator light 180 can be interrupted by activity such as from a customer or banker wherein the light sources 102 and the indicator light 180 are turned OFF prior to having been ON for the duration of the designated sanitization period to operate in the interrupted mode of operation by the controller 600. Some examples of actions that will interrupt or stop the automatic sanitization mode of operation to stop the light source 102 and the indicator light 180 from emitting light include: opening and/or closing the teller door of the teller unit 302, pressing the customer send or call button, opening the customer door of the customer unit 202, recalling the carrier 204 to the customer unit 202, pressing the teller recall button, and/or recalling the carrier 204 to the teller unit 302. Activating the night or sanitizing lock switch 306 will also stop the light source 102 from emitting light and stop the automatic sanitization mode of operation. In one form, the carrier 204 is positioned in the carrier pocket 200 of the customer unit 202 during the automatic sanitization mode of operation when the automatic sanitization mode of operation is interrupted or stopped to recall the carrier 204 to the teller unit 302. In one form, activation of the night or sanitizing lock switch 306 also stops the light source 102 from emitting light, optionally recalls the carrier 204 to the teller unit 302, and optionally locks the light source 102 from further operation. Therefore, during the interrupted mode, the light function of the light source 102 does not operate for the entire duration of the designated sanitization period.

Alternatively, the light kit assembly 100 is operable in a manual sanitization mode of operation such that the customer or banker initiates the sanitization of the carrier 204. During the manual sanitization mode of operation, the night or sanitizing lock switch 306 is activated to turn ON. The controller 600 will then operably control the carrier 204 in the customer unit 202 or send the carrier 204 to the customer unit 202. The customer door may be open or closed. If the customer unit door is open, the controller 600 will operably close the customer door and the light source 102 and the indicator light 180 will turn ON for the designated sanitization period. In one form, the designated sanitization period is three (3) minutes however in other embodiments the designated sanitization period is longer or shorter. To interrupt or stop the light source 102 from emitting light for the entire designated sanitization period, the night or sanitizing lock switch 306 is turned OFF and the light source 102 and the indicator light 180 are turned OFF. The carrier 204 is then recalled to the teller unit 302 before the night or sanitizing lock switch 306 is turned ON to avoid the light source 102 and the indicator light 180 being turned ON. After the period of time of inactivity, the lane will go into normal night mode by sending the carrier 204 to the teller unit 302 and locking the light kit assembly 100.

The present disclosure may comprise one or more of the following features and combinations thereof.

According to one embodiment of the present disclosure, a light kit assembly for sanitizing a carrier in a drive-through banking system, comprising: a mounting plate having a back wall that extends between a first bi-fold wing and a second bi-fold wing, wherein the first bi-fold wing includes a first portion and a second portion with a first wing angle there between, and wherein the second bi-fold wing includes a first portion and a second portion with a second wing angle there between; a first UV light source assembled with one of the first portion or the second portion of the first bi-fold wing; and a second UV light source assembled with one of the first portion or the second portion of the second bi-fold wing.

In a further embodiment, one of the first or second portions of the first bi-fold wing includes a plurality of light holes; and the first UV light source includes a plurality of UVC lamps, wherein the plurality of UVC lamps is assembled with the plurality of light holes of the first or second portions of the first bi-fold wing such that the plurality of UVC lamps emit light through the plurality of light holes. In a further embodiment, the plurality of UVC lamps includes UVC LEDs.

In a further embodiment, one of the first or second portions of the second bi-fold wing includes a plurality of light holes; and the second UV light source includes a plurality of UVC lamps, wherein the plurality of UVC lamps is assembled with the plurality of light holes of the first or second portions of the second bi-fold wing such that the plurality of UVC lamps emit light through the plurality of light holes. In a further embodiment, the plurality of UVC lamps includes UVC LEDs.

In a further embodiment, the back wall and the first portion of the first bi-fold wing includes a first backwall angle there between such that the first portion opens away from the back wall, and wherein the back wall and the first portion of the second bi-fold wing includes a second back-wall angle there between such that the first portion opens away from the back wall.

In a further embodiment, the back wall has a length that is longer than a length of the first bi-fold wing or a length of the second bi-fold wing.

In a further embodiment, the back wall has a length that is shorter than a length of the first bi-fold wing or a length of the second bi-fold wing.

In a further embodiment, further comprising: one or more power supply assemblies operably connected to the first and the second UV light sources.

According to yet another embodiment of the present disclosure, a method for sanitizing a carrier in a drive-through banking system having a customer station operatively coupled to a teller station wherein the carrier moves between the customer and teller stations, comprising: providing a light kit assembly having one or more UV light sources mounted on a mounting plate in one of the customer station or the teller station, the light kit assembly operatively coupled to a controller, wherein the controller is structured to control operation of the one or more UV light sources; locating the carrier in the one customer station or the teller station that includes the light kit assembly therein; closing a door of the one customer station or the teller station that contains the carrier and the light kit assembly; and operating the one or more UV light sources via the controller when the carrier and the light kit assembly are in the one customer station or the teller station such that UV wavelength light from the one or more light sources is directed towards the carrier for a designated sanitization period.

In a further embodiment, the operating the one or more light sources includes operating the light kit assembly in either an automatic sanitization mode of operation or a manual sanitization mode of operation.

In a further embodiment, the automatic sanitization mode of operation includes closing the door of the one customer station or the teller station after a period of time of inactivity of the customer unit.

In a further embodiment, the automatic sanitization mode of operation includes closing the door of the one customer station or the teller station after a designated number of uses of the customer station by one or more customers.

In a further embodiment, the operating the one or more light sources includes operating the light kit assembly in an interrupted mode of operation, wherein the interrupted mode of operation includes ceasing the one or more light sources from emitting light.

In a further embodiment, the manual sanitization mode of operation includes: activating a sanitizing lock switch operably connected to the teller unit; sending the carrier to the customer station; closing the door of the customer station that contains the carrier and the light kit assembly; and operating the one or more light sources via the controller such that UV wavelength light from the one or more light sources is directed towards the carrier for a designated sanitization period.

In a further embodiment, the designated sanitization period is about three minutes.

In a further embodiment, the light kit assembly includes an indicator light that emits light during the designated sanitization period.

According to yet another embodiment of the present disclosure, a light kit subassembly for sanitizing a carrier in a drive-through banking system that includes a customer station operatively coupled to a teller station wherein the carrier moves between the customer and teller stations, the light kit subassembly comprising: a light kit assembly including a mounting plate assembled with a first UV light source and a second UV light source, the mounting plate having a back wall that extends between a first bi-fold wing and a second bi-fold wing, wherein the first bi-fold wing includes a first portion and a second portion with a first wing angle there between, and wherein the second bi-fold wing includes a first portion and a second portion with a second wing angle there between, wherein the first UV light source is assembled with one of the first portion or the second portion of the first bi-fold wing, wherein the second UV light source is assembled with one of the first portion or the second portion of the second bi-fold wing; and a carrier pocket sized to receive the light kit assembly therein, the carrier pocket further sized and configured for installation in one of the customer or the teller stations.

In a further embodiment, one of the first or second portions of the first bi-fold wing includes a plurality of light holes, the first UV light source includes a plurality of UVC LEDs, wherein the plurality of UVC LEDs is assembled with the plurality of light holes of the first or second portions of the first bi-fold wing such that the plurality of UVC LEDs emit light through the plurality of light holes, and wherein one of the first or second portions of the second bi-fold wing includes a plurality of light holes, the second UV light source includes a plurality of UVC LEDs, wherein the plurality of UVC LEDs is assembled with the plurality of light holes of the first or second portions of the second bi-fold wing such that the plurality of UVC LEDs emit light through the plurality of light holes.

In a further embodiment, the light kit assembly includes a second mounting plate assembled with a third UV light source similar to the first UV light source, the second mounting plate assembled with a fourth UV light source similar to the second UV light source, wherein the first and the second mounting plates are positioned in a mirror-image arrangement in the carrier pocket to enable 360 degree application of UV light onto the carrier.

While the invention has been illustrated and described in detail in the drawings and foregoing description, the same is to be considered as illustrative and not restrictive in character, it being understood that only certain exemplary embodiments have been shown and described. Those skilled in the art will appreciate that many modifications are possible in the example embodiments without materially departing from this invention. Accordingly, all such modifications are intended to be included within the scope of this disclosure as defined in the following claims.

In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that no claim element herein is to be construed under the provisions of 35 U.S.C. § 112(f), unless the element is expressly recited using the phrase "means for." The schematic flow chart diagrams and method schematic diagrams described above are generally set forth as logical flow chart diagrams. As such, the depicted order and labeled steps are indicative of representative embodiments. Other steps, orderings and methods may be conceived that are equivalent in function, logic, or effect to one or more steps, or portions thereof, of the methods illustrated in the schematic diagrams. Further, reference throughout this specification to "one embodiment", "an embodiment", "an example embodiment", or similar language means that a particular feature, structure, or characteristic described in connection with the embodiment is included in at least one embodiment of the present invention. Thus, appearances of the phrases "in one embodiment", "in an embodiment", "in an example embodiment", and similar language throughout this specification may, but do not necessarily, all refer to the same embodiment.

Additionally, the format and symbols employed are provided to explain the logical steps of the schematic diagrams and are understood not to limit the scope of the methods illustrated by the diagrams. Although various arrow types and line types may be employed in the schematic diagrams, they are understood not to limit the scope of the corresponding methods. Indeed, some arrows or other connectors may be used to indicate only the logical flow of a method. For instance, an arrow may indicate a waiting or monitoring period of unspecified duration between enumerated steps of a depicted method. Additionally, the order in which a particular method occurs may or may not strictly adhere to the order of the corresponding steps shown. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

What is claimed is:

1. A light kit assembly for sanitizing a carrier in a drive-through banking system, comprising:
    a mounting plate having a back wall that extends between a first bi-fold wing and a second bi-fold wing, wherein the first bi-fold wing includes a first portion and a second portion with a first wing angle there between, and wherein the second bi-fold wing includes a first portion and a second portion with a second wing angle there between;
    a first UV light source assembled with one of the first portion or the second portion of the first bi-fold wing; and
    a second UV light source assembled with one of the first portion or the second portion of the second bi-fold wing.

2. The light kit assembly of claim 1, wherein one of the first or second portions of the first bi-fold wing includes a plurality of light holes; and
    the first UV light source includes a plurality of UVC lamps, wherein the plurality of UVC lamps is assembled with the plurality of light holes of the first or second portions of the first bi-fold wing such that the plurality of UVC lamps emit light through the plurality of light holes.

3. The light kit assembly of claim 2, wherein the plurality of UVC lamps includes UVC LEDs.

4. The light kit assembly of claim 1, wherein one of the first or second portions of the second bi-fold wing includes a plurality of light holes; and
    the second UV light source includes a plurality of UVC lamps, wherein the plurality of UVC lamps is assembled with the plurality of light holes of the first or second portions of the second bi-fold wing such that the plurality of UVC lamps emit light through the plurality of light holes.

5. The light kit assembly of claim 4, wherein the plurality of UVC lamps includes UVC LEDs.

6. The light kit assembly of claim 1, wherein the back wall and the first portion of the first bi-fold wing includes a first backwall angle there between such that the first portion opens away from the back wall, and
    wherein the back wall and the first portion of the second bi-fold wing includes a second backwall angle there between such that the first portion opens away from the back wall.

7. The light kit assembly of claim 1, wherein the back wall has a length that is longer than a length of the first bi-fold wing or a length of the second bi-fold wing.

8. The light kit assembly of claim 1, wherein the back wall has a length that is shorter than a length of the first bi-fold wing or a length of the second bi-fold wing.

9. The light kit assembly of claim 1, further comprising:
    one or more power supply assemblies operably connected to the first and the second UV light sources.

10. A method for sanitizing a carrier in a drive-through banking system having a customer station operatively coupled to a teller station wherein the carrier moves between the customer and teller stations, comprising:
    providing a light kit assembly having one or more UV light sources mounted on a mounting plate in one of the customer station or the teller station, the light kit assembly operatively coupled to a controller, wherein the controller is structured to control operation of the one or more UV light sources;
    locating the carrier in the one customer station or the teller station that includes the light kit assembly therein;
    closing a door of the one customer station or the teller station that contains the carrier and the light kit assembly; and
    operating the one or more UV light sources via the controller when the carrier and the light kit assembly are in the one customer station or the teller station such that UV wavelength light from the one or more light sources is directed towards the carrier for a designated sanitization period.

11. The method of sanitizing the carrier of claim 10, wherein the operating the one or more light sources includes operating the light kit assembly in either an automatic sanitization mode of operation or a manual sanitization mode of operation.

12. The method of sanitizing the carrier of claim 11, wherein the automatic sanitization mode of operation includes closing the door of the one customer station or the teller station after a period of time of inactivity of the customer unit.

13. The method of sanitizing the carrier of claim 11, wherein the automatic sanitization mode of operation includes closing the door of the one customer station or the teller station after a designated number of uses of the customer station by one or more customers.

14. The method of sanitizing the carrier of claim 11, wherein the operating the one or more light sources includes operating the light kit assembly in an interrupted mode of operation, wherein the interrupted mode of operation includes ceasing the one or more light sources from emitting light.

15. The method of sanitizing the carrier of claim 11, wherein the manual sanitization mode of operation includes:
    activating a sanitizing lock switch operably connected to the teller unit;
    sending the carrier to the customer station;
    closing the door of the customer station that contains the carrier and the light kit assembly; and operating the one or more light sources via the controller such that UV wavelength light from the one or more light sources is directed towards the carrier for a designated sanitization period.

16. The method of sanitizing the carrier of claim 10, wherein the designated sanitization period is about three minutes.

17. The method of sanitizing the carrier of claim 10, wherein the light kit assembly includes an indicator light that emits light during the designated sanitization period.

18. A light kit subassembly for sanitizing a carrier in a drive-through banking system that includes a customer station operatively coupled to a teller station wherein the carrier moves between the customer and teller stations, the light kit subassembly comprising:
  a light kit assembly including a mounting plate assembled with a first UV light source and a second UV light source, the mounting plate having a back wall that extends between a first bi-fold wing and a second bi-fold wing, wherein the first bi-fold wing includes a first portion and a second portion with a first wing angle there between, and wherein the second bi-fold wing includes a first portion and a second portion with a second wing angle there between, wherein the first UV light source is assembled with one of the first portion or the second portion of the first bi-fold wing, wherein the second UV light source is assembled with one of the first portion or the second portion of the second bi-fold wing; and
  a carrier pocket sized to receive the light kit assembly therein, the carrier pocket further sized and configured for installation in one of the customer or the teller stations.

19. The light kit subassembly of claim 18, wherein one of the first or second portions of the first bi-fold wing includes a plurality of light holes, the first UV light source includes a plurality of UVC LEDs, wherein the plurality of UVC LEDs is assembled with the plurality of light holes of the first or second portions of the first bi-fold wing such that the plurality of UVC LEDs emit light through the plurality of light holes, and
  wherein one of the first or second portions of the second bi-fold wing includes a plurality of light holes, the second UV light source includes a plurality of UVC LEDs, wherein the plurality of UVC LEDs is assembled with the plurality of light holes of the first or second portions of the second bi-fold wing such that the plurality of UVC LEDs emit light through the plurality of light holes.

20. The light kit subassembly of claim 18, wherein the light kit assembly includes a second mounting plate assembled with a third UV light source similar to the first UV light source, the second mounting plate assembled with a fourth UV light source similar to the second UV light source, wherein the first and the second mounting plates are positioned in a mirror-image arrangement in the carrier pocket to enable 360 degree application of UV light onto the carrier.

* * * * *